(12) United States Patent
Truwit

(10) Patent No.: US 6,267,769 B1
(45) Date of Patent: Jul. 31, 2001

(54) TRAJECTORY GUIDE METHOD AND APPARATUS FOR USE IN MAGNETIC RESONANCE AND COMPUTERIZED TOMOGRAPHIC SCANNERS

(75) Inventor: Charles L. Truwit, Wayzata, MN (US)

(73) Assignee: Regents of the Universitiy of Minnesota, Minneapolis, MN (US)

( * ) Notice: Subject to any disclaimer, the term of this patent is extended or adjusted under 35 U.S.C. 154(b) by 0 days.

(21) Appl. No.: 09/058,092

(22) Filed: Apr. 9, 1998

Related U.S. Application Data

(63) Continuation-in-part of application No. 08/919,649, filed on Aug. 28, 1997, now abandoned, which is a continuation-in-part of application No. 08/856,664, filed on May 15, 1997, now abandoned.

(51) Int. Cl.$^7$ .................................................. A61B 19/00
(52) U.S. Cl. ............................... 606/130; 606/129; 606/1
(58) Field of Search .................................. 606/53, 56, 59, 606/72, 79, 80, 87, 96, 102, 129, 130, 1, 108

(56) References Cited

U.S. PATENT DOCUMENTS

| | | |
|---|---|---|
| 1,664,210 | 3/1928 | Hall . |
| 2,119,649 | 6/1938 | Roosen . |
| 2,135,160 | 11/1938 | Beekhuis ................................. 23/239 |

(List continued on next page.)

OTHER PUBLICATIONS

Allison, S., et al., "Microchannel Plate Intensifier Response in Transverse Magnetic Field", *Electronic Letters*, 26, 770–771, (Jun. 7, 1990).

Gillies, G., et al., "Magnetic Manipulation Instrumentation for Medical Physics Research", *Review of Scientific Instruments*, 65, 533–562, (1994).

Grady, M., et al., "Initial Experimental Results of a New Stereotaxic Hyperthermia System", *American College of Surgeons: 1998 Clinical Congress: Surgical Forum, 39*, 507–509, (1998).

(List continued on next page.)

*Primary Examiner*—David O. Reip
(74) *Attorney, Agent, or Firm*—Schwegman, Lundberg, Woessner & Kluth, P.A.

(57) ABSTRACT

A surgical method and apparatus for accurately aligning the trajectory of, guiding of, and introducing or withdrawal of an instrument includes a base with a movable member. The base has a tubular shape. Positioned near the first end of the base is a seat. The seat is dimensioned to receive a movable member. A positioning member is used to move the movable member. The initial position of the movable member is determined using a scanning device, such as a CT scanner, frameless stereotaxy device or an MRI device. The movable member is elevated above the patient so that a burr hole does not have to be made in the patient to do the above described procedure. The second end has an opening therein and the tubular body is positioned between the seat and the second end. A flange near the second end is used to attach the base to the patient. The flange may also engage a plastic ring such that it can rotate or swivel with respect to the ring. The ring is attached to a flexible adhesive patch so which may be attached to the body. A portion or the entire positioning stem may be doped to make the positioning stem detectable by x-radiation and by the CT scanner. Arched bails can also be attached to the base for adjusting the trajectory alignment. An adapter externalizes burr holes and eliminates the need for burr hole. The externalizer forms a substitute burr hole away from the skull or body so tools which usually work only within a burr hole can be used without having to make a burr hole.

33 Claims, 17 Drawing Sheets

U.S. PATENT DOCUMENTS

| | | |
|---|---|---|
| 3,017,887 * | 1/1962 | Heyer . |
| 3,055,370 | 9/1962 | McKinney et al. . |
| 3,055,371 | 9/1962 | Kulick et al. . |
| 3,273,559 | 9/1966 | Evans . |
| 3,282,152 | 11/1966 | Myer ........................................ 88/24 |
| 3,672,352 | 6/1972 | Summers . |
| 4,355,645 | 10/1982 | Mitani et al. . |
| 4,448,195 | 5/1984 | LeVeen et al. . |
| 4,571,750 | 2/1986 | Barry .................................. 623/258 |
| 4,572,198 | 2/1986 | Codrington . |
| 4,608,977 | 9/1986 | Brown . |
| 4,660,563 | 4/1987 | Lees . |
| 4,665,928 | 5/1987 | Linial et al. . |
| 4,755,642 | 7/1988 | Parks .................................. 200/283 |
| 4,791,934 | 12/1988 | Brunnett . |
| 4,793,355 | 12/1988 | Crum et al. . |
| 4,805,615 | 2/1989 | Carol . |
| 4,807,620 | 2/1989 | Strul et al. . |
| 4,824,436 | 4/1989 | Wolinsky .............................. 604/53 |
| 4,869,247 | 9/1989 | Howard, III et al. . |
| 4,896,673 | 1/1990 | Rose et al. . |
| 4,902,129 | 2/1990 | Siegmund et al. ................... 356/241 |
| 4,922,924 | 5/1990 | Gambale et al. . |
| 4,955,891 | 9/1990 | Carol ................................... 606/130 |
| 4,957,481 | 9/1990 | Gatenby ............................... 604/20 |
| 4,986,280 | 1/1991 | Marcus et al. . |
| 4,986,281 | 1/1991 | Preves et al. . |
| 4,989,608 | 2/1991 | Ratner . |
| 4,998,938 | 3/1991 | Ghajar et al. ........................ 606/130 |
| 5,024,236 | 6/1991 | Shapiro . |
| 5,052,329 | 10/1991 | Bennett ............................... 116/209 |
| 5,057,106 | 10/1991 | Kasevich et al. ...................... 606/33 |
| 5,065,761 | 11/1991 | Pell . |
| 5,078,140 | 1/1992 | Kwoh . |
| 5,078,142 | 1/1992 | Siczek et al. . |
| 5,087,256 | 2/1992 | Taylor et al. .......................... 606/28 |
| 5,099,846 | 3/1992 | Hardy . |
| 5,102,402 | 4/1992 | Dror et al. ............................ 604/265 |
| 5,116,345 | 5/1992 | Jewell et al. .......................... 606/130 |
| 5,120,322 | 6/1992 | Davis et al. ........................... 604/265 |
| 5,125,888 | 6/1992 | Howard et al. ........................ 600/12 |
| 5,142,930 | 9/1992 | Allen et al. ............................ 74/469 |
| 5,143,086 | 9/1992 | Duret et al. . |
| 5,154,179 | 10/1992 | Ratner . |
| 5,166,875 | 11/1992 | Machida ......................... 364/413.13 |
| 5,171,217 | 12/1992 | March et al. .......................... 604/53 |
| 5,174,297 | 12/1992 | Daikuzono . |
| 5,211,165 | 5/1993 | Dumoulin et al. . |
| 5,230,338 | 7/1993 | Allen et al. . |
| 5,257,998 | 11/1993 | Ota et al. ............................. 606/130 |
| 5,279,309 | 1/1994 | Taylor et al. . |
| 5,290,266 | 3/1994 | Rohling et al. ....................... 604/272 |
| 5,291,890 | 3/1994 | Cline et al. . |
| 5,305,203 | 4/1994 | Raab ............................. 364/413.13 |
| 5,309,913 | 5/1994 | Kormos et al. . |
| 5,330,485 | 7/1994 | Clayman et al. ..................... 606/130 |
| 5,375,596 | 12/1994 | Twiss et al. . |
| 5,383,454 | 1/1995 | Bucholz . |
| 5,445,166 | 8/1995 | Taylor . |
| 5,470,307 | 11/1995 | Lindall ................................... 604/20 |
| 5,494,655 | 2/1996 | Rocklage et al. .................... 424/9.36 |
| 5,515,160 | 5/1996 | Schulz et al. ........................ 356/241 |
| 5,517,990 | 5/1996 | Kalfas et al. . |
| 5,528,652 | 6/1996 | Smith et al. ........................... 378/65 |
| 5,638,819 | 6/1997 | Manwaring et al. . |
| 5,647,361 | 7/1997 | Damadian . |
| 6,006,126 * | 12/1999 | Cosman ............................... 600/426 |
| 6,021,343 * | 2/2000 | Foley et al. ........................... 600/429 |

OTHER PUBLICATIONS

Grady, M., et al., "Magnetic Stereotaxis System for Neurosurgical Procedures", *Proc. 37th International Instrumentation Symp.*, San Diego, CA, 665–675, (May 1991).

Grady, M., et al., "Magnetic Stereotaxis: A Technique to Deliver Stereotactic Hypertherma", *Neurosurgery, 27*, 1010–1016, (Dec. 1990).

Grady, M., et al., "Nonlinear Magnetic Stereotaxis: Three–Dimensional, in vivo Remote Magnetic Manipulation of a Small Object in Canine Brain", *Medical Physics, 17*, 405–415, (1990).

Grady, M., et al., "Preliminary Experimental Investigation of in vivo Magnetic Manipulation: Results and Potential Application in Hyperthermia", *Medical Physics, 16*, 263–272, (Mar. 1989).

Hata, N., et al., "Needle Insertion Manipulator for CT– and MR– Guided Stereotactic Neurosurgery", *In: Interventional MR: Techniques and Clinical Experience*, F. Jolesz and I. Young, eds., 99–106.

Howard, M., et al., "Magnetic Movement of a Brain Thermoceptor", *Neurosurgery, 24*, 444–448, (Mar. 1989).

Howard, M., et al., "Magnetic Neurosurgery", *Stereotactic and Functional Neurosurgery, 66*, 102–107, (1996).

Howard, M., et al., "Magnetic Neurosurgery: Image–Guided, Remote–Controlled Movement of Neurosurgical Implants", *Ch. 26 In: Clinical Neurosurgery; Proceedings of the Congress of Neurological Surgeons*, San Francisco, CA, 382–391, (1995).

Howard, M., et al., "Review of Magnetic Neurosurgery Research", *J. Image Guided Surgery, 1*, 295–299, (Nov. 1995).

Lawson, M., et al., "Near Real–Time Bi–planar Fluoroscopic Tracking System for the Video Tumor Fighter", *SPIE, 1445*, 265–275, (1991).

McNeil, R., et al., "Characteristics of an Improved Magnetic–Implant Guidance System", *IEEE Trans. on Biomedical Engineering, 42*, 802–808, (Aug. 1995).

McNeil, R., et al., "Functional Design Features and Initial Performance Characteristics of a Magnetic–Implant Guidance System for Stereotactic Neurosurgery", *IEEE Trans. on Biomedical Engineering, 42*, 793–801, (Aug. 1995).

Meeker, D., et al., "Optimal Realization of Arbitrary Forces in a Magnetic Stereotaxis System", *IEEE Trans. on Magnetics, 32*, 320–328, (Mar. 1996).

Molloy, J., et al., "Experimental Determination of the Force Required for Insertion of a Thermoseed into Deep Brain Tissues", *Annals of Biomedical Engineering,18*, 299–313, (1990).

Molloy, J., et al., "Thermodynamics of Movable Inductively Heated Seeds for the Treatment of Brain Tumors", *Medical Physics, 18*, 794–803, (1991).

Quate, E., et al., "Goniometric Motion Controller for the Superconducting Coil in a Magnetic Stereotaxis System", *IEEE Trans. on Biomedical Eng., 38*, 899–905, (Sep. 1991).

Ramos, P., et al., "Electro–Optic Imaging Chain for a Biplanar Fluoroscope for Neurosurgery: Magnetic Field Sensitivity and Contrast Measurements", *Optical Engineering, 32 (SPIE)* 1644–1656, (Jul. 1993).

Ramos, P., et al., "Low–Dose, Magnetic Field–Immune, Bi–Planar Fluoroscopy for Neurosurgery", *Proc. SPIE, 1443 (Medical Imaging V: Image Physics)*, 160–170, (1991).

Ramos, P., et al., "Microchannel Plate Image Intensifier Electron Dynamics in Magnetic Field", *Electronic Letters, 27*, 1636–1638, (Aug., 29, 1991).

Ritter, R., et al., "Magnetic Stereotaxis: An Application of Magnetic Control Technology to the Needs of Clinical Medicine", *Proc. of the MAG'95 Industrial Conf. and Exhibition*, Technomic Pub. Co., Lancaster, PA., Allaire. P., ed., 186–193, (1995).

Ritter, R., et al., "Magnetic Stereotaxis: Computer–Assisted, Image–Guided Remote Movement of Implants in the Brain", *Ch. 26 In: Computer–Integrated Surgery; Technology and Clinical Applications*, MIT Press, Cambridge, MA., Taylor, R., et al., eds., 363–369, (1996).

Ritter, R., et al., "Stereotaxie Magnetique: Deplacement D'Implants dans le Cerveau, Assistes par Ordinateur et Guides par Imagerie.", *Innovation et Technologie en Biologie et Medecine, 13*, 437–449, (1992).

Szikora, I., et al., "Endovascular Treatment of Experimental Aneurysms with Liquid Polymers: The Protective Potential of Stents", *Neurosurgery, 38*, 339–347, (Feb. 1996).

* cited by examiner

TRAJECTORY GUIDE METHOD AND APPARATUS FOR USE IN MAGNETIC RESONANCE AND COMPUTERIZED TOMOGRAPHIC SCANNERS

CROSS-REFERENCE TO RELATED APPLICATIONS

This application is a continuation-in-part of U.S. patent application Ser. No. 08/919,649, filed Aug. 28, 1997, now abandoned, which in turn is a continuation-in-part of U.S. patent application Ser. No. 08/856,664, filed May 15, 1997, now abandoned.

FIELD OF THE INVENTION

The present invention is related to a surgical working platform. More specifically, the present invention relates to a platform and method for using the same for facilitating the alignment of surgical and observational instruments, and for the passing of said instruments into a patient using a drill hole. The present invention may be adapted for use in a MR scan or CT scan environment.

BACKGROUND OF THE INVENTION

In the treatment of some diseases or defects associated with a patient, it has been found necessary to access specific targets within a patient. In the treatment of some diseases of or defects of human beings, it has been found necessary to access specific portions of the brain. Currently there are several methods for inserting surgical and observational instruments into a patient's brain.

U.S. Pat. No. 3,055,370 issued to McKinney et al. shows one currently used method for placing a surgical instrument to access a specific portion of the brain. The surgical instrument of the U.S. Pat. No. 3,055,370 patent includes a ball which has a bore. The direction of the bore can be changed. The instrument has an elongated tube of a specific length. A stylet is inserted within the tube to access the globus pallidus and perform a pallidotomy. An opening or burr hole is made in the skull at a specific landmark on the skull. Next, X-rays are taken in the fore-and-aft (AP) and lateral positions, and the line of the bar is projected downwardly by a ruler both in the fore-and-aft (AP) and lateral positions, so that the direction of the needle can be determined before it is inserted. When the direction of the longitudinal axis of the tubular member is determined to be satisfactory, a holder is threaded further into a tap to force a surface against a ball and lock a tubular member into place. Alignment of the trajectory is not measurable along a specific line occurring at the intersection of two planes. Alignment is dependent on placement of the burr hole at a specific location to determine one plane. X-rays are used to determine another plane-based use of common landmarks on the skull. The end result is that an educated guess is being used to position the stylet at the globus pallidus for the pallidotomy. One shortcoming with the method of using X-ray imaging to direct a surgical or observational instrument, is that many of the destinations within a patient are not viewable via X-ray. Another shortcoming relates to the slight shifting of intracranial contents, once a burr hole is placed and the dura and arachnoid are penetrated. Once cerebrospinal fluid is released via the burr hole, the intracranial contents (i.e. brain) may shift one or more millimeters. In such a case, the calculated trajectory is no longer accurate. Hence, there is an inherent inaccuracy with the described scheme.

Several other methods are also used to place instruments, catheters, or observational tools into patients. Like the method discussed above, most surgical procedures are performed through craniotomy flaps or craniotomy burr holes. A burr hole is an round opening in the skull having a diameter of about 14 mm. The diameter is a standard length in most parts of the world. Currently, the Europeans use a slightly different standard diameter of about 15 mm. Needles or probes are typically passed through the burr hole into the brain using framed stereotaxy, frameless stereotaxy or freehand without stereotaxy. Many instruments used for doing various operations attach to the burr hole. Many use an outside thread that grips the inner diameter of the burr hole.

The freehand method depends very heavily on the knowledge and judgment of the surgeon. In the freehand method, the surgeon determines the insertion point with a couple of measurements from a known landmark. The surgeon then looks at the measured point, makes adjustments, determines the angle of insertion and then inserts the surgical instrument or tool.

In framed stereotaxy, a ring frame is mounted to the patient's skull by multiple (typically three or four) pins or screws. This ring frame is used to determine a three dimensional data set. From this data set, Cartesian coordinates are calculated for both the lesion, the location of the pins or screws, and the fiducial marks on the frame. The ring frame fits into a large frame. A large frame is then attached to the patient in the operating suite. The large frame provides known positions and guides the surgical or observational instruments. The large frame is used to position the instrument to be introduced into the patient through a burr hole so that it intersects the target. In frameless stereotaxy, the ring frame is replaced with several markings on the patient's skull which can be used to determine several known positions. The large frame is replaced by a camera. The camera is usually infrared or some such device. Multiple sensors readable by the camera are placed on the instrument. For example, the surgical instrument or tool is provided with one or more light emitting diodes ("LEDs") which are tracked by the camera. The position of the surgical instrument can be calculated from the information from the LEDs on the surgical instrument or observational tool.

U.S. Pat. Nos. 4,955,891 and 4,805,615, both issued to Carol, each discuss the use of stereotaxy surgery with computerized tomographic ("CT") scanning. CT scanning is used to determine the exact position of a lesion or specific portion of the brain. After the exact position of the lesion or specific portion of the brain is determined, a phantom fixture is set up. The phantom fixture replicates the position of the ring frame on the patient. A phantom target is set up. The phantom fixture and target are typically determined outside the operating suite. Within the operating suite, the instrument can then be positioned on the phantom fixture such that it intersects the target. The information from the phantom fixture can then be used to initially position the instrument in the operating suite. Most procedures require forming a burr hole in the patient's head. Loss of fluid from the burr hole results in a shifting of the contents of the cranial cavity. The burr hole is typically made in the operating suite after the phantom frame and target have been set up. As a result, a subsequent CT scan is necessary especially in the case when the target is small, thereby requiring accurate placement of the instrument.

U.S. Pat. No. 4,998,938 issued to Ghajar et al. shows another surgical device for facilitating the insertion of an instrument into a patient's cranial cavity through a burr hole. The device includes a guide having an end configured to pass into the burr hole. There is a separate locking member. A body member includes alignment markings to help with insertion of a catheter or stylet. Unlike U.S. Pat. No. 3,055,370, there is no movable member for adjusting the path of the guide.

The methods currently in use all have a number of shortcomings. One of the shortcomings is that all of the techniques require initially making craniotomy flaps or craniotomy burr holes in the patients skull or body. A burr hole of about 14 mm is made in the skull. Needles or probes are typically passed through the burr hole into the brain during a typical procedure, such as a biopsy or laser ablation of a tumor. The burr hole formed is large and it takes a fair amount of surgical time to make. In addition to the surgical time, the forming of the burr hole results in shifting of the contents within the cranial cavity. It would be advantageous if a surgical tool would allow surgical procedures to be performed without the formation of a burr hole. In addition, it would be advantageous if tools that attached or required a burr hole could be adapted so that the surgical procedure would not require formation of the burr hole in the patient's skull. The formation of a burr hole is a time consuming portion of an operation.

Most of the techniques currently used to place a surgical instrument or observational tool within a patient employ a limited amount of accuracy. In particular, current framed, frameless, and freehand methods compute or predict trajectories on the basis of imaging data or anatomic landmarks that do not account for the slight, but real shifting of the brain upon opening the cranium and meninges to the level of the subarachnoid space. This inherent inaccuracy inherently limits the success of these various methodologies. In other words, these systems do not use any means of updating the data files to include data obtained following the placement of a surgical burr hole and opening of the meninges. In addition, all the methods require large amounts of judgment on the part of the surgeon placing the surgical instrument or tool, and in particular, offer no direct feedback on the success or failure of the trajectory to reach the target. Very few of the techniques use an imaging or scanning apparatus to aid in the placement of the surgical instrument or observational tool. The only one that does requires a phantom frame and target to be set up to simulate the real geometry. In short, none of the apparatuses appear to use an imaging or scanning apparatus as extensively as they could be used to minimize the time and effort needed to accurately place a surgical instrument into a patient, and to offer immediate data on the success or failure of the trajectory to reach the target. It would be advantageous if more accurate methods could be developed which could use either MR or computerized tomographic ("CT") scanners. Both MR or CT scanners are widely available worldwide. Even though CT scanning equipment has the disadvantage of patient exposure to x-radiation, a method for accurate placement of an instrument using CT scanning equipment would be even more widely available to patients around the world than a similar MR method.

SUMMARY OF THE INVENTION

An externalizer eliminates the need for always making a burr hole when placing an instrument within the skull of the patient. In one embodiment, the externalizer is integral with a positioning stem. In another embodiment, the externalizer forms a universal burr hole away from the patient's body. This embodiment is an adapter which can accommodate any tool which previously required a burr hole. The externalizer forms a substitute burr hole away from the skull or body of the patient. The result is that any instrument that normally requires a burr hole, can now be used with the externalizer.

The making of a burr hole within the patient's skull is now optional. Many procedures can now be accomplished by making a screw or drill opening in the patient's body. The drill or screw opening is much smaller than a burr hole. This procedure requires much less time and results in less shifting of contents within the cranial cavity since there is less fluid loss.

A surgical method and apparatus for accurately aligning the trajectory of, guiding of, and introducing or withdrawal of an instrument using CT scanning equipment is also disclosed. The apparatus is doped with barium or another dopant so that it is CT visible. The apparatus includes a base which has a movable member movably attached to the base. The movable member has a passage therein which forms a portion of the trajectory path. The movable member also includes a guide stem which has an opening therein. The guide stem is attached to said movable member such that the opening in the guide stem substantially aligns with the passage in the movable member. The movable member can include either an integral guide stem for holding the positioning stem or a removably attached guide stem. In the case of the former, a positioning stem is inserted into the opening of the integral guide stem for purposes of trajectory alignment. In the case of the latter, the removably attached guide stem can be removed and replaced with a positioning stem. A portion or the entire positioning stem may be doped to make the positioning stem detectable by x-radiation and by the CT scanner. The base of the trajectory guide includes two arched bails which are used to adjust the trajectory alignment.

In operation, the positioning stem is initially positioned. A CT scan is performed to locate the positioning stem and the target. The line formed by the positioning stem is determined by the CT scanning system. Another line between the end of the positioning stem nearest the patient and the target is then determined by the computer of the CT scanning system. The second line between the end of the positioning stem nearest the patient and the target corresponds to or is coaxial with the trajectory. The computer of the CT scanning system determines the difference between these lines and produces an adjustment that the surgeon must make to reposition the positioning stem so that it aligns with the trajectory corresponds to a line passing through the opening in the ball and guide stem. The adjustment corresponds to the grid increments or markings on two arched bails of the trajectory guide. Another scan is done to confirm alignment. If not aligned, several of the above steps are repeated until alignment is attained.

Advantageously, widely available CT scanning devices used for diagnostic purposes can be employed to place an instrument within the body of a patient. There is no need for framed stereotaxy or unframed stereotaxy, two procedures which require large amounts of time to perform. Procedures that formerly required many hours can now be performed in substantially less amounts of time with the trajectory guide. Other procedures which required a burr hole can also be performed in less time.

Although frameless stereotaxy is not required, if the equipment for frameless stereotaxy is available, the procedure associated with positioning the positioning stem is simpler when compared to the CT only method.

The externalizer can be used with CT scanning equipment, frameless stereotaxy equipment or with MR equipment. The various equipment is used to align the positioning stem or instrument with a target within the body. The externalizer can also be used to perform procedures with or without a burr hole. The externalizer adapter also provides this option for instruments which normally require the formation of a burr hole.

An externalizer can also be adapted for use on other portions of the body. The body portal type externalizer is usually used to direct surgical instruments to larger targets within the body. The body portal type externalizer features an angled or vertical base that swivels or rotates within a plastic ring. The plastic ring is merged with an adhesive patch that is used to attach the body portal type externalizer to the body. The angled base allows surgical instruments to be passed through the externalizer without interfering with nearby objects, such as a magnet, in an operating suite. The alternative vertical base is an option for an open magnet MR device. The swivel or ability to rotate the base allows the surgeon or technician access from a comfortable position with respect to the body portal. An incision is made in the patient and the body portal type externalizer is placed over the incision. The adhesive patch seals the area. After the instrument is removed and the procedure is completed, the body portal type externalizer is removed and the incision is stitched or bandaged.

BRIEF DESCRIPTION OF THE DRAWINGS

For a better understanding of the present invention, reference may be made to the accompanying drawings in which:

FIG. 7b is a cutaway side view of the locking member of the trajectory guide, along line 7b—7b of FIG. 7a.

DESCRIPTION OF THE EMBODIMENT

In the following detailed description of the embodiment, reference is made to the accompanying drawings which form a part hereof, and in which is shown by way of illustration specific preferred embodiments in which the invention may be practiced. These embodiments are described in sufficient detail to enable those skilled in the art to practice the invention, and it is to be understood that other embodiments may be utilized and that structural, logical and electrical changes may be made without departing from the spirit and scope of the present invention. The following detailed description is, therefore, not to be taken in a limiting sense, and the scope of the present invention is defined only by the appended claims.

Figure 2:
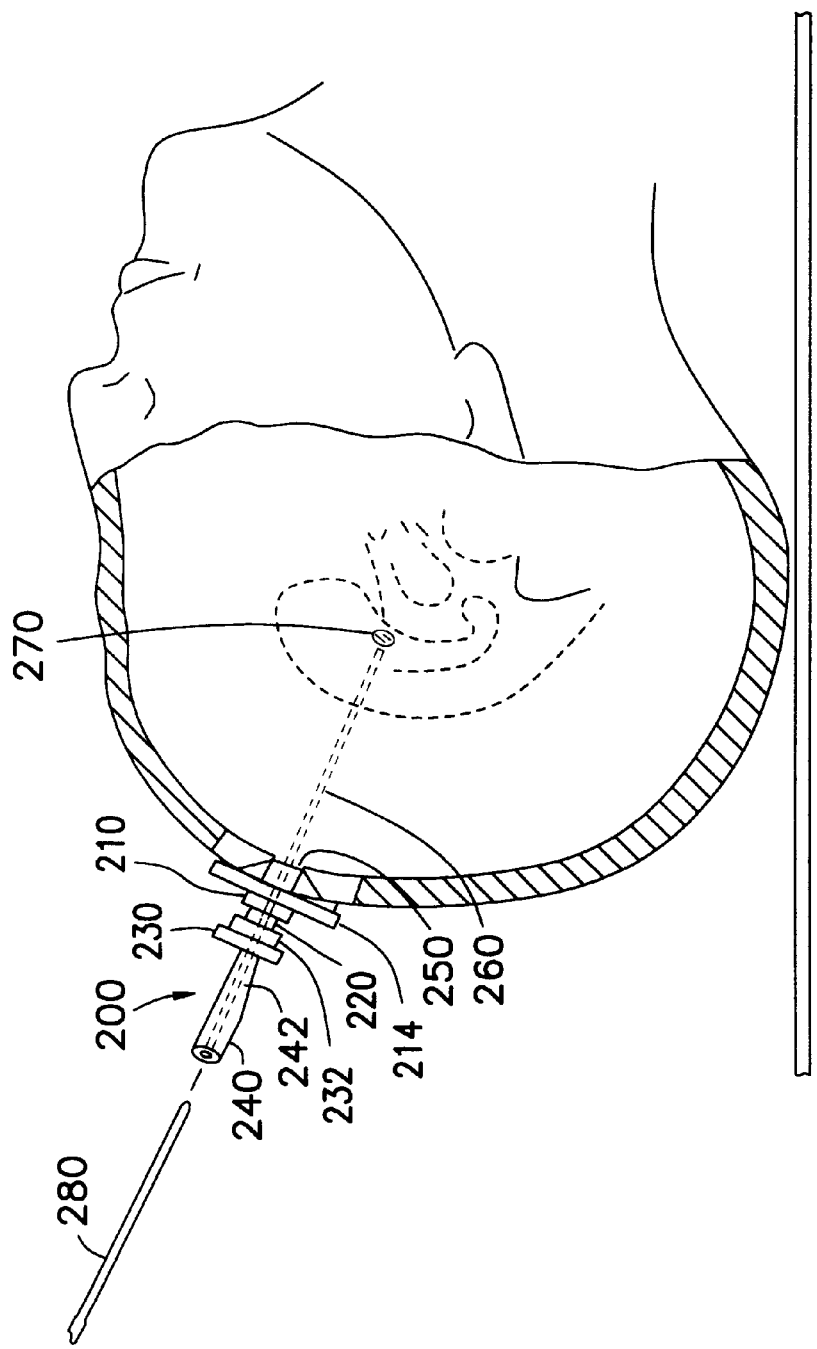
FIG. 2 is a side view of a patient on which the trajectory guide is being used.

Within some parts of a patient, it is critical to very accurately place a surgical instrument. For example, in neurosurgery, it is very critical to have instruments, such as catheters or needles, placed very accurately within the cranium or head of a patient. FIG. 2 shows a side view of a patient on which a trajectory guide 200 is being used. The trajectory guide 200 includes a base unit 210, a movable member 220, a locking member 230 and a guide stem 240. The base unit 210 is attached to the skull of the patient. In the particular embodiment shown, the attachment is made by way of bone screws. A burr hole is not required in the patient. In this particular embodiment, the movable member 220 is held away from the patient's body such that a burr hole is not required.

The movable member 220 has a passage therein 222 which is shown in FIG. 2 as dotted lines. The guide stem 240 also has an elongated opening 242 therein. The opening 242 is also shown as dotted lines in FIG. 2. The passage 242 in the guide stem 240 and the opening 222 in the movable member or ball 220 form a line or a trajectory 260 which, when the guide stem 240 and movable member 220 are positioned correctly, intersects with a target 270 within the patient. The guide stem 240 and movable member or ball 220 form the first part of the trajectory 260. The base unit 210 includes a seat 218 or socket which allows the movable member 220 to move freely. The seat is positioned away from a flange 214 on the base 210. The seat 218 is elevated with respect to the flange 214. Below the seat is an opening through which instruments may pass. The elevated seat 218 and opening below serve as a substitute for a burr hole in the skull.

After aligning the opening 242 and the opening 222 to form the trajectory 260, a twist drill is then used to make a small opening in the patient. The twist drill is passed through the opening 242 and opening 222 along trajectory 260. After a drill hole is formed in the patient, a surgical instrument or observational tool can be inserted into the opening 242 of the guide stem 240 and passed through the passage in the movable member 220 and through the drill hole formed along the trajectory 260. Further insertion of the surgical instrument or observational tool into the patient for a selected distance will strike or place the tool near or at the target 270. The opening 242 in the guide stem 240 and the passage 222 in the movable member 220 guide a surgical instrument along the trajectory 260 to the target 270. Of course, the movable member 220 is locked into place by locking member 230 before a surgical instrument 280 is placed through the opening 242 in the guide member 240.

Figure 3:
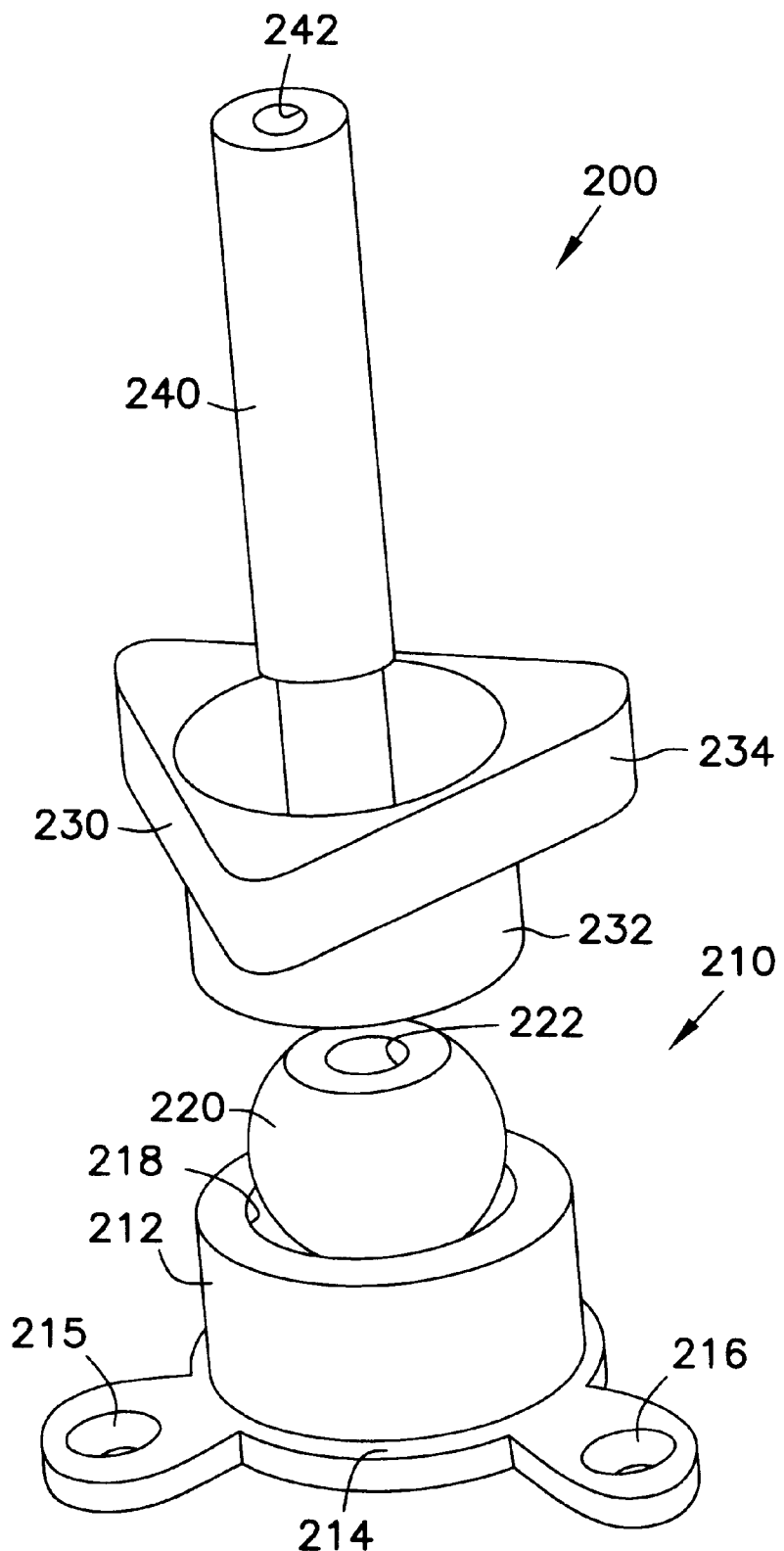
FIG. 3 is an exploded isometric view of the trajectory guide with a removably attached guide member installed.

FIG. 3 shows an exploded isometric view of the trajectory guide 200 with a guide member installed. As shown in FIG. 3, the trajectory guide 200 is comprised of a base 210, a movable member 220, a locking member 230, and the guide member 240. The guide member 240 may be threadably attached or the guide member can be made integral with the movable member 220. The base 210 includes a cylindrical portion 212 and a flange 214. The flange looks like a series of ears. Each of the ears of the flange 214 includes a plurality of countersunk screw openings 215, 216, and 217. The countersunk screw openings 215, 216, and 217 receive bone screws which are screwed into the skull bone or the bone of a patient. The flange 214 also includes markings 219 used to position the guide member 240. As shown in FIG. 3, the markings 219 are in the form of a grid having an x-axis and a y-axis. The cylindrical portion 212 fits within the burr hole 250 in the patient. The base also includes a semi-spherical seat 218 on the end of the base opposite the flange 214. The flange 214 is in a plane away from the seat 218. Although not shown in FIG. 3, there is an opening in the base 210 having a first end which terminates at the seat 218 and another end which terminates at the bottom of the base 210. This opening is essentially a substitute burr hole.

As shown in FIG. 3, the movable member 220 is essentially a spherical member or a ball. The spherical member or ball fits within the seat 218. The spherical member or ball moves freely within the seat 218. The ball-shaped movable member 220 also has an opening therein 222. The opening passes through the ball shaped movable member. One end of the opening may have a set of internal threads therein, which can be used to receive mating threads which are placed onto the guide stem or member 240 or positioning stem (discussed with respect to FIG. 4).

The locking member 230 also has an opening therethrough. The locking member 230 includes a cylindrical bottom portion 232 and a flange 234. The opening through the locking member 230 has sufficient space to allow movement of movable member 220 when the locking member is in an unlocked or untightened position. Although not shown in FIG. 4, the bottom of the cylindrical portion 232 of the locking member 230 includes a set of internal threads. The set of internal threads engage a set of external threads on the base unit 210 (shown in FIG. 7b). As will be detailed later, when the internal threads of the locking member 230 are engaged with the threads on the base 210, a portion of the locking member engages the movable member 220 to fix the movable member and the passage 222 therethrough at a fixed position.

A guide stem or guide member 240 is also shown in FIG. 3. The guide stem has an elongated opening 242 therein. The elongated opening passes through the length of the guide stem 240. One end of the guide stem includes a set of external threads which engage the internal threads of the spherical, movable member 220. When the external threads of the guide stem 240 engage the internal threads of the movable member 220, the opening 242 is substantially aligned with the passage 222 in the movable member. The opening 242 and passage 222 form the first part or guide for the trajectory 260 to the target 270 within the patient. It should be noted that the movable member 220 need not necessarily be a spherical element, although the spherical shape allows the ball to have a universal joint type swivel action which is preferred. As mentioned previously, the movable element 220 and the guide stem 240 can be formed as one piece. This would eliminate the need for the threaded end of the guide stem 240 and the threaded inner diameter 222 of the movable member 220.

In addition, the locking member 230 can be formed in most any shape. A flange 234 is useful in that it allows additional leverage for tightening or loosening the locking member. Any shape capable of being turned or placed into a locking position with respect to the movable member 220 is acceptable.

Positioning Member

Figure 4:
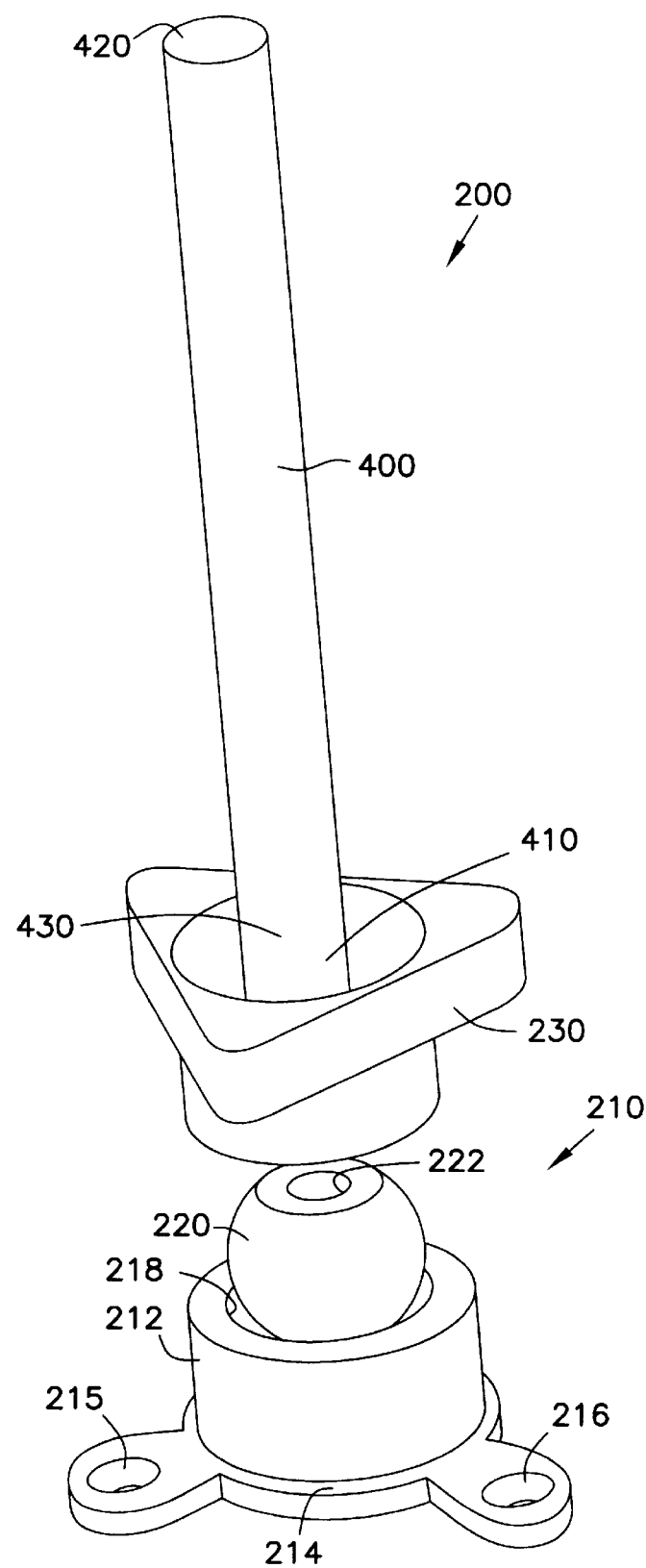
FIG. 4 is an exploded isometric view of the trajectory guide with a removably attached positioning member installed.

Now turning to FIG. 4, an exploded isometric view of the trajectory guide 200 with a positioning member 400 is shown. The positioning member 400 may also be referred to as a positioning stem. Many of the parts of the trajectory guide 200 shown in FIG. 4 are the same as those shown in FIG. 3. In the interest of time, a discussion of the common elements will not be repeated. Several of the basic elements will be numbered for the purposes of this discussion. The difference between FIGS. 3 and 4 is that the guide stem or guide member 240 has been replaced with the positioning stem 400. The positioning stem 400 includes an end 410 which carries threads for engaging internal threads within the passage 222 in the movable element 220.

Movable Member

Figure 5A:
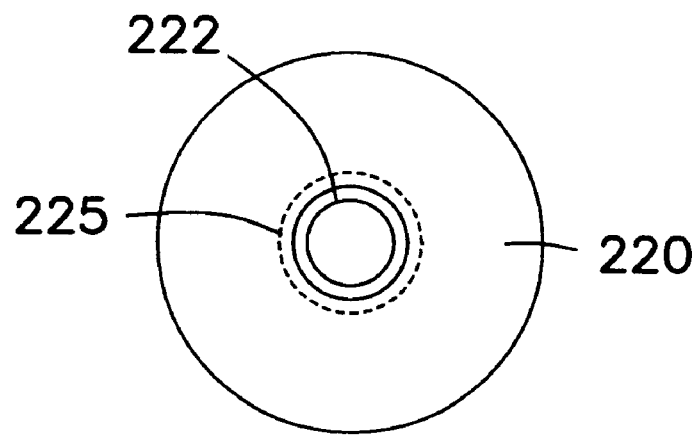
FIG. 5a is a top view of the movable member or ball of the trajectory guide.
Figure 5B:
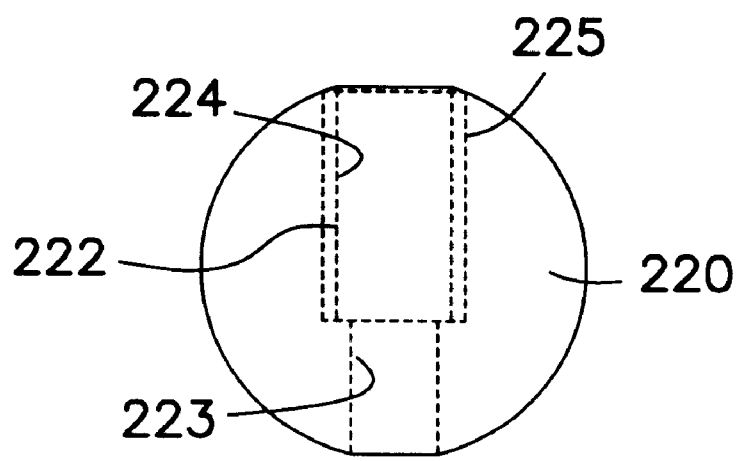
FIG. 5b is a side view of the movable member or ball of the trajectory guide.

FIGS. 5a and 5b show the movable member which will now be discussed in slightly more detail. FIGS. 5a and 5b show that the movable member 220 is substantially spherical in shape. The movable member 220 has an opening 222 therein. The opening 222 includes a smaller diameter portion 223 and a larger diameter portion 224. The inside surface of the larger portion 224 of opening 222 is threaded as indicated by reference numeral 225. The larger diameter portion 224 and the threads 225 receive the external threaded portion of either the positioning stem 400 or the guide stem 240. The smaller diameter portion 223 of the opening 222 is of a sufficient diameter to allow an instrument, such as a needle, probe, catheter, endoscope, or electrode to pass through the opening. The movable member 220 is made of a biocompatible material such as delrin.

Figure 6B:
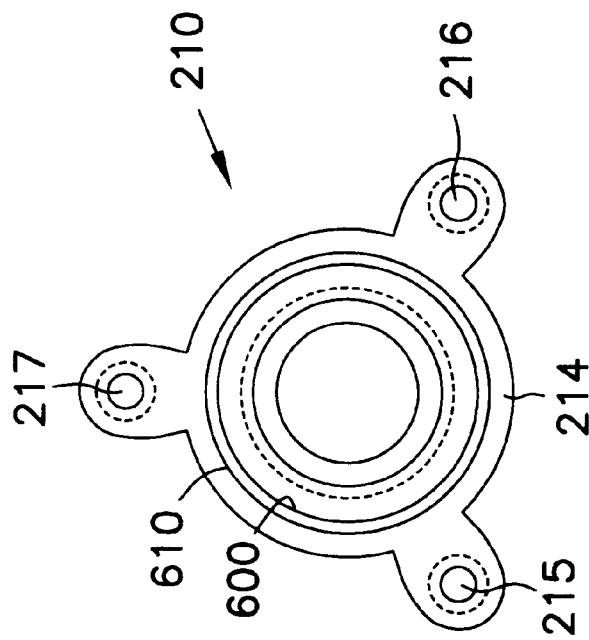
FIG. 6b is a top view of the base of the trajectory guide.
Figure 6A:
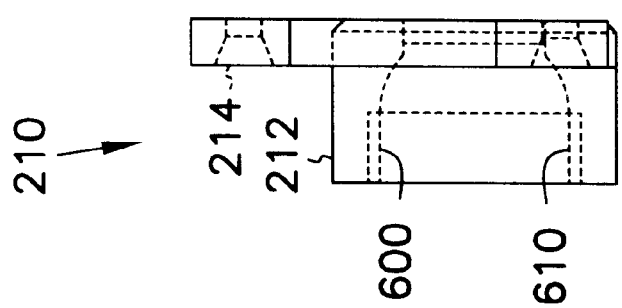
FIG. 6a is a side view of the base of the trajectory guide.
Figure 9:
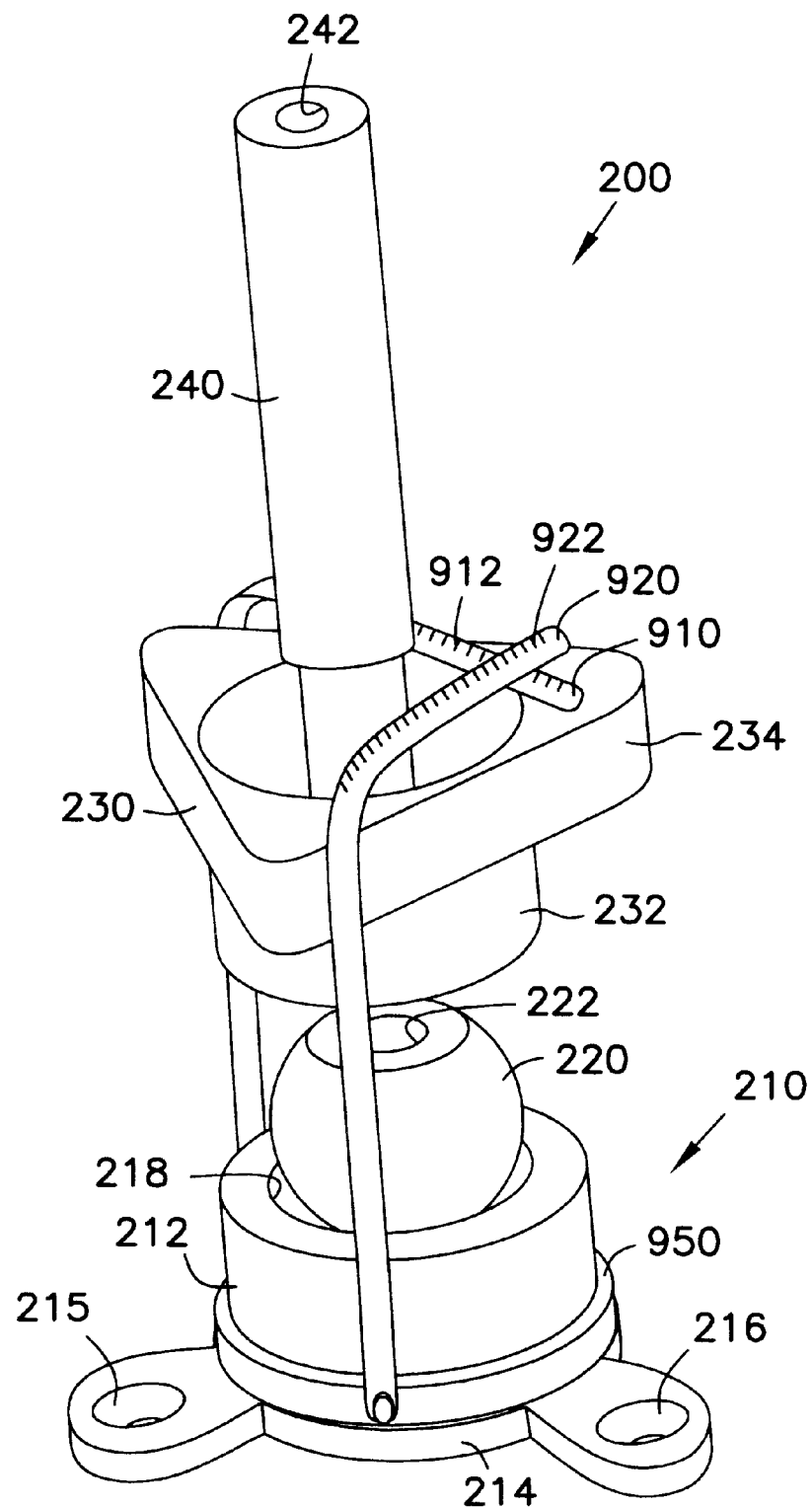
FIG. 9 is an isometric view of another preferred embodiment of the trajectory guide having arched positioning bails.
Figure 10:
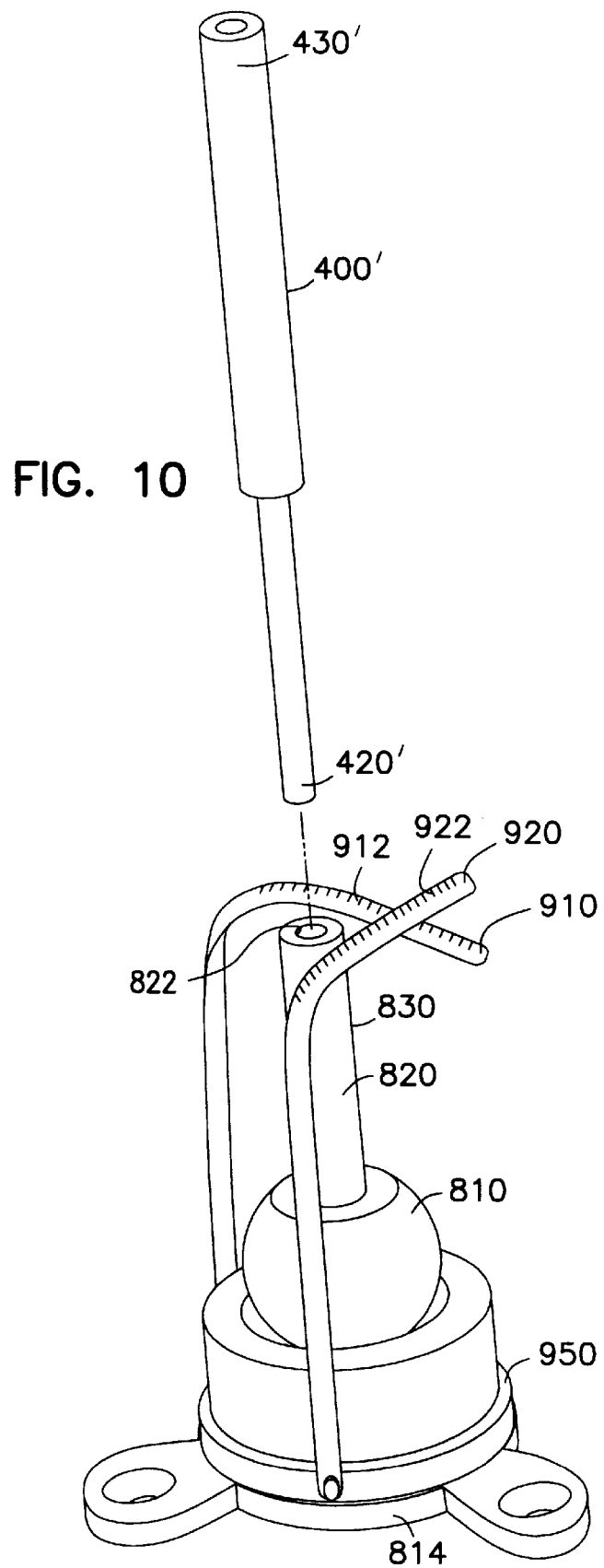
FIG. 10 is an isometric view of yet another preferred embodiment of the trajectory guide having arched positioning bails.

FIGS. 6a and 6b show a side and top view of the base 210 of the trajectory guide 200. The base 210 includes the cylindrical portion 212 and the flange 214. The flange 214 includes ears with countersunk openings 215, 216, and 217 as well as the seat 218 which receives the movable member 220. It should be noted that the flange 214 can be of any shape. As shown, the seat 218 is in a plane substantially parallel to the plane of the flange 214. The seat 218 is elevated with respect to the flange 214. The seat 218 is on one end of the base 210 and the flange 214 is on the opposite end of the base 210. Between the seat and the flange is an opening 600 which includes an internally threaded portion 610. The internally threaded portion 610 is dimensioned so as to receive the threads of either the positioning stem 400 or the guide stem 240. The flange 214 may include a first arched bail 910 and a second arched bail 920 (arched bails are shown in FIGS. 9 and 10) which are used to align the positioning stem 400 so that it defines a trajectory 260 which intersects the target 270 within the patient. It should be noted, that although the flange 214 is shown as having a triangular shape, the flange could be most any shape.

Figure 7B:
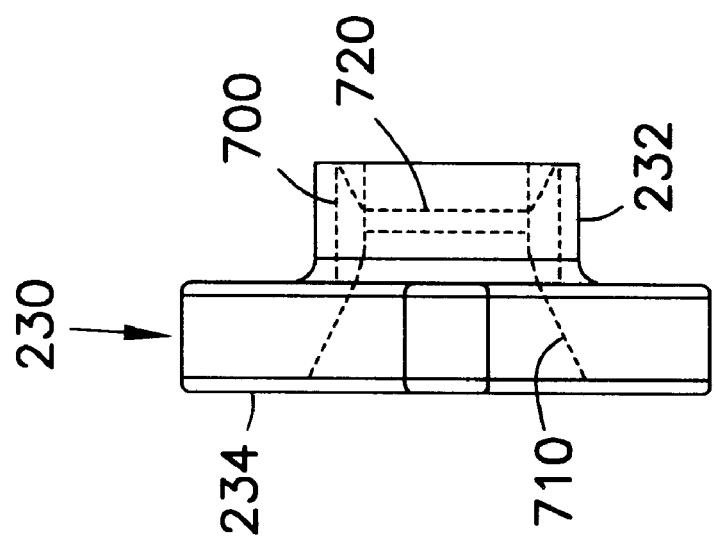
Figure 7A:
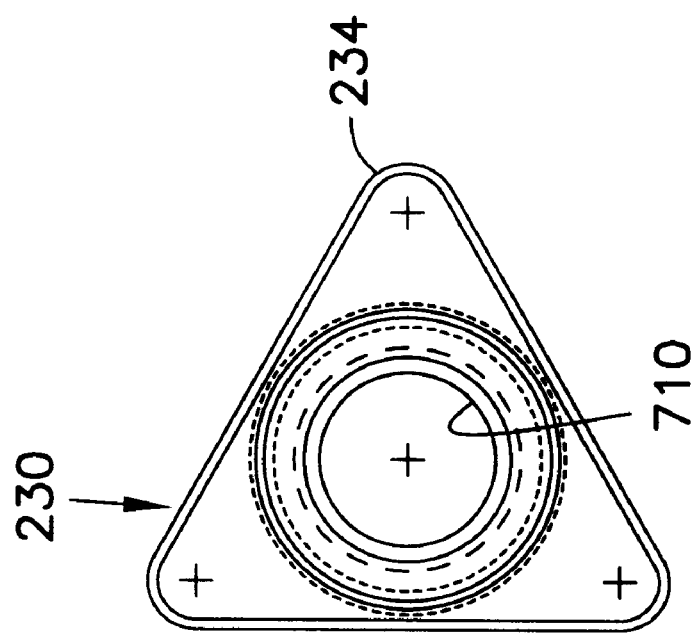
FIG. 7a is a top view of the locking member of the trajectory guide.

Now turning to FIGS. 7a and 7b, the locking member of the trajectory guide 200 will now be discussed. The locking member 230 includes the cylindrical portion 232 and a flange 234. The external surface of the flange 232 is threaded to form a threaded external surface 700. The threads associated with the externally threaded surface 700 are dimensioned so as to engage the internally threaded surface 600 of the base 210. The locking member 230 also includes an opening 710 which passes through the locking member 230. The locking member also has a locking surface 720. In this particular embodiment, the locking surface 720 is flat so that it engages a flat face on the movable member 220. The flanges 234 are extended so that the threads of the threaded surface 700 can be easily engaged with the internal threads 600 of the base 210. It is contemplated that other geometric shapes could be used for the locking member and that other locking surfaces could be employed.

Integral Guide Stem and Movable Member

Figure 8:
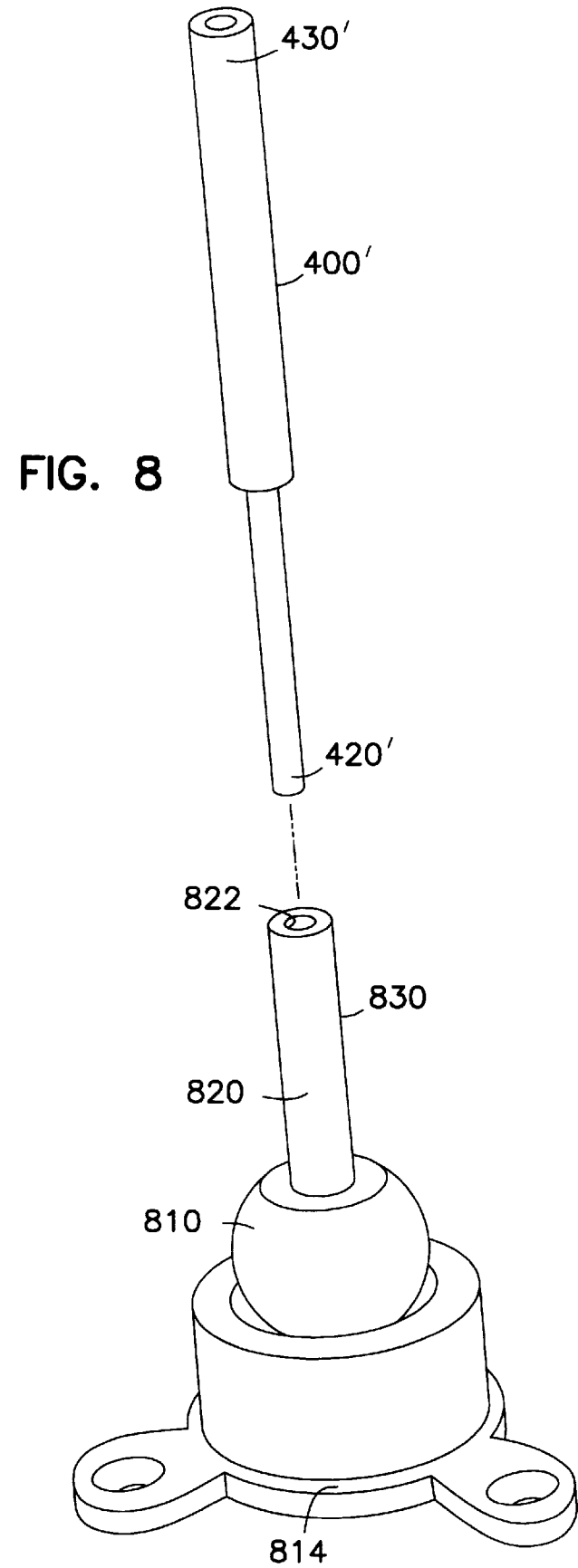
FIG. 8 is an isometric view of another preferred embodiment of the trajectory guide.

FIG. 8 shows an isometric view of a movable element 820 that has a ball end 810 and a guide stem end 830. The movable element 820 fits within the base 210 and locking member 230. As shown, the movable element 820 has a passageway 822 therein which traverses the length of the movable element 820. In other words, the passageway 822 passes through the guide stem end 830 and through the ball end 810. FIG. 8 also shows a positioning stem 400. The positioning stem 400 is dimensioned so that it fits snugly within the passageway 822.

The various guide stems and positioning stems shown in FIGS. 2–8 can be used with any type of body scanner. The positioning stems can be provided with MR viewable portions and positioned with the aid of an MR imaging device similar to the one discussed in the U.S. patent application entitled "Surgical Instrument Trajectory Guide Method and Apparatus" filed Aug. 28, 1997 and having Ser. No. 08/919, 649. The guide stems shown in FIGS. 2–8 can also be adapted for use with a CT scanner. CT scanners are widely available around the world.

CT Scanner

Figure 1:
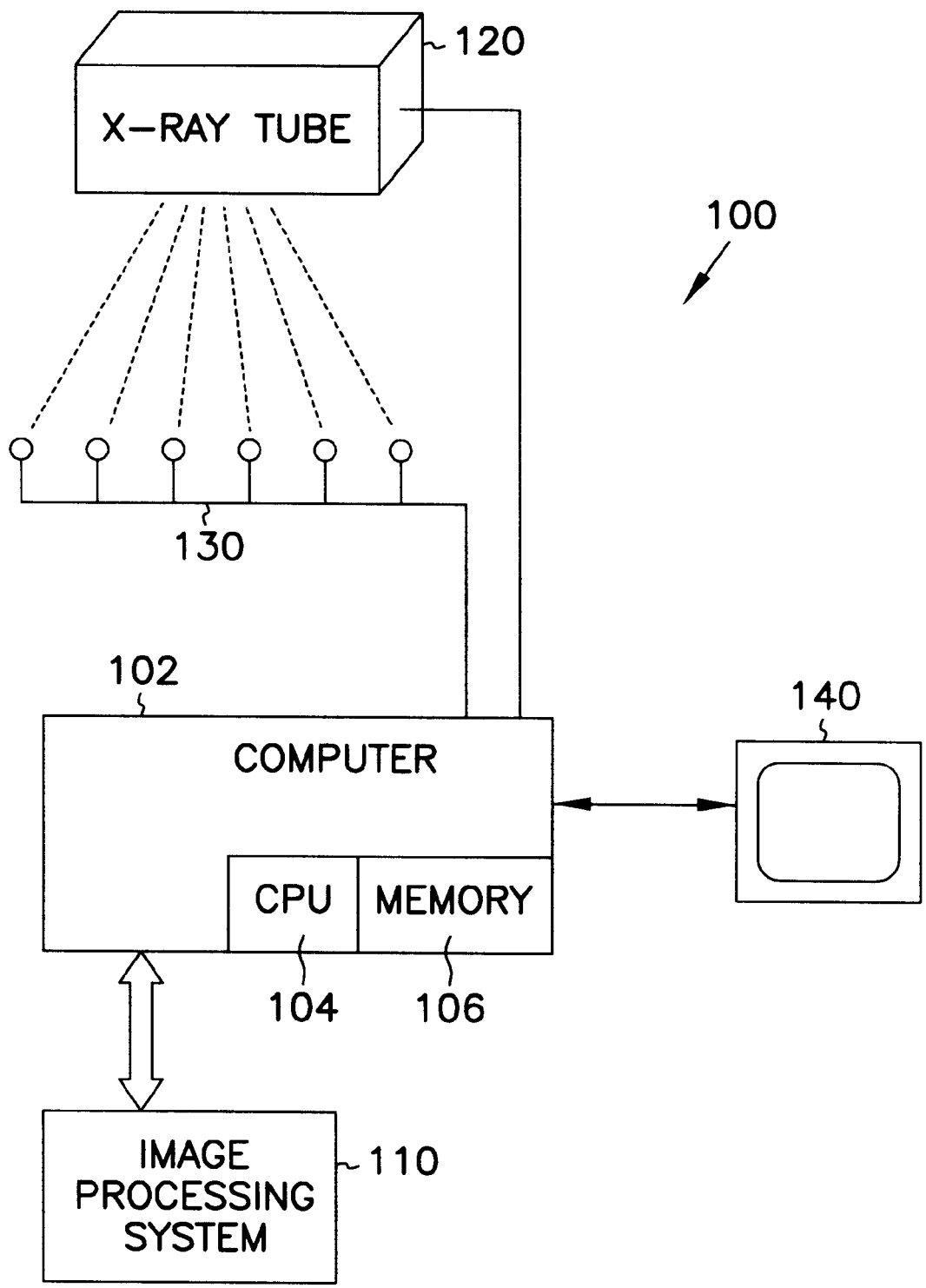
FIG. 1 is a block diagram of a patient scanning system.

FIG. 1 is a block diagram of a patient scanning system 100. The specific scanning system shown is a computerized tomography ("CT") system. An CT scanning system 100 includes a computer 102. The computer 102 includes a central processing unit ("CPU") 104 and memory 106. The CPU 104 and memory 106 has the capacity to perform multiple calculations used to determine images as well as positions of various organs, or portions or within an image field. The computer 102 controls an image data processing portion 110. The computer 102 also reconstructs an image along a desired plane. An X-ray tube 120 is pulsed at many times per second. Across from the x-ray tube are a plurality of detectors 130. Most commonly, the detectors 130 are photo diodes.

The data is interpreted and placed on a display 140 associated with the computer of the CT system 100. The computer 102 and the CPU 104 and memory 106 can use data acquired from the CT system 100 to build up images of a portion of the patient which is being subjected to x-radiation. The images are typically referred to as slices. For example, a horizontal slice and a vertical slice can be made of the portion of the body or patient being imaged. The computer can also recalculate and build other slices for use by doctors and radiologists having any selected orientation needed to facilitate study of various items within a patient. For example, lesions can be found within the body as well as certain organs. Different slices can be requested to facilitate study of these targets. From the data acquired, the position of the lesions or organs can also be very accurately determined using a Cartesian or polar coordinate system.

In operation, x-ray beams of a computerized tomography scanner pass through a human body or an object and are collected with an array of detectors; the beam is rotated to produce the equivalent of a "slice" through the area of interest. The x-ray information collected during the rotation is then used by a computer to reconstruct the "internal structures," and the resulting image is displayed on a television screen. This technique represents a noninvasive way of seeing internal structures, and has in many ways revolutionized diagnostic approaches. In the brain, for example, computerized tomography can readily locate tumors and hemorrhages, thereby providing immediate information for evaluating neurological emergencies.

Basically, the scanner gantry is composed of an x-ray tube, an array of detectors opposite the tube, and a central aperture in which the person (or object) is placed. X-rays are generated in short bursts, usually lasting 2–3 ms; the x-ray beam contains an "invisible image" of the internal structures. The role of the detectors is to collect this information, which is then fed into a computer. The computer reconstructs the image from the information collected by the detectors. In order to obtain enough information to calculate one image, the newer scanners can take as many as 90,000 readings (300 pulses and 300 detectors). CT scanning devices are widely available throughout the world. The above description of the CT scanning device 100 is simply for demonstrative purposes.

For use with CT scanning system 100, the positioning stem 400 of FIG. 4 is modified by doping with a dopant that is detectable with x-radiation. The dopant can be a liquid carrying barium which is housed with a tubular cavity of the position stem. The dopant can also be made within the material of the positioning stem. Since it is detectable, the positioning stem 400 is viewable as a result of the CT scan. One dopant which could be used is barium. The entire positioning stem 400 or selected portions of the positioning stem may be doped so as to produce a detectable image on the display 180 of the CT scanning device 100. For example, rather than dope the entire positioning stem 400, the ends 420 and 430 of the positioning stem may be doped. The two ends of the positioning stem could be detected by the CT scanning device 100 and used to define a line corresponding to the current trajectory through the opening 222 in the movable member 220.

Now turning to FIG. 9, the further modification of the device shown in FIG. 4 will be discussed. The modifications provide for an alignment instrument which can be used where only CT scanners are available. In the alternative, if CT scanning equipment is available, it can be used as an alternative to more expensive methods, such as MR scanning. The positioning stem 400 is doped as discussed above. A ring 950 is attached to the cylindrical portion 212 of the base 210. The ring 950 moves with repsect to the cylindrical portion 212. Attached to the ring 950 is a first arched bail 910 and a second arched bail 920. The arched bails 910 have physical markings 912 thereon. The arched bail 920 has physical markings 922 thereon. At least one of the bails 910 or 920 is also doped at least three points so that the three points determine a plane viewable on a CT scan. The arched bails 910 and 920 are secured to the flange 214 with a fastener which can be securely tightened to prevent movement of the bail 910 and 920. The bails 910 and 920 are also made so that they extend a distance above the movable member 220 to allow clearance for the locking member 230.

Also for use with a CT scanning system 100, the positioning stem 400' of the trajectory guide 200', shown in FIG. 8 is doped with a dopant that is detectable with x-radiation. Since it is detectable, the positioning stem 400' is viewable as a result of the CT scan. One dopant which could be used is barium. The entire positioning stem 400' or selected portions of the positioning stem may be doped so as to produce a detectable image on the display 180 of the CT scanning device 100. For example, rather than dope the entire positioning stem 400', the ends 420' and 430' of the positioning stem may be doped. The two ends of the positioning stem could be detected by the CT scanning device 100 and used to define a line corresponding to the current trajectory through the opening guide member end 830 and the opening 822 in the ball end 220.

The first end 420 and the second end 430' of the positioning stem 400' do not need to be doped with the same material. This may enable the computer 102 associated with the CT scanning device to more easily discern end 420' from end 430'. In this embodiment, the positioning stem 400' is inserted into the guide stem end 830. The movable member 820 and more specifically the opening 822 in the movable member 820 is moved until it is aligned to the desired trajectory 260 to the target 270. Once aligned, a locking member 230 (not shown in FIG. 8 to more clearly illustrate this embodiment) locks the ball end 810 in place. The positioning stem 400' is removed and the surgical instrument is passed into the guide member end.

In still another embodiment, portions of the movable member 820 are doped with a dopant that makes it x-radiation readable and viewable. Movable member 820 includes a ball as well as an extended guide stem end 830. All or part of the guide stem end 830 may be doped. The ends of the opening 822 in the movable member 820 may also be doped. The ends could then be used in locating the line or trajectory 260 defined by the opening 822. In this embodiment, there would be no real need for positioning stem 400'. When the movable member 820 is determined to be properly aligned, the movable member 820 would be locked into place and the surgical instrument or tool would be passed directly into the opening 822.

FIG. 10 shows the trajectory guide 200' having a base 210 that has a ring 950. The arched bail 910 and the arched bail 920 are attached to the ring 950. The arched bails are attached to the ring 950 so that they can be rotatably moved with respect to the base 210. The bails 910 and 920 can then be rotated with respect to the ring 950. The attachment also allows them to be tightened so the bails 910 and 920 stay in one position. The bails 910 and 920 are positioned so that there is clearance so the locking member 230 can be loosened to adjust the position of the at least one of the bails 910 or 920. At least one of the bails 910 or 920 includes a CT readable portion that defines a plane. Preferably, one edge of the bail, 910 or 920, will be readable via CT scan. The edge of the bail 910 or 920 will be an arcuate line which defines a plane. The bail 910 will have markings 912 and the bail 920 will have markings 922. The bails 910 and 912 would enable a person to reposition the movable member 820 to make adjustments to the trajectory guide so that the opening 822 in the movable member aligns with the trajectory 260.

Method for Using CT Scans and Trajectory Guide

In operation, a patient undergoes a CT scan with a CT scanning device 100 to locate a particular organ within a patient or to locate lesions or any other target 270 within the patient. It should be noted that targets are not necessarily limited to being within the head of a patient. There can also be other areas of a patient where it would be critical to accurately place a surgical or observational tool. In addition, it should also be noted that the patient need not necessarily be human. A patient may include any living animal.

Once the target 270 is found and located using the CT scanning system 100, the base 210 of the trajectory guide 200 can be attached to the patient. The base is affixed to the patient in an area near the target 270. The computer 102 of the scanning device 100 is used to determine the exact location of the target 270. The exact location can be found in any type of coordinate system, although normally a Cartesian coordinate system is used. Once the base 210 is attached to the patient, the remaining portions of the trajectory guide 200 are attached to the base 210. In other words, the movable member 220, the locking guide, the locking member 230 and a positioning stem 400 are added to form a complete trajectory guide 200.

Figure 11:
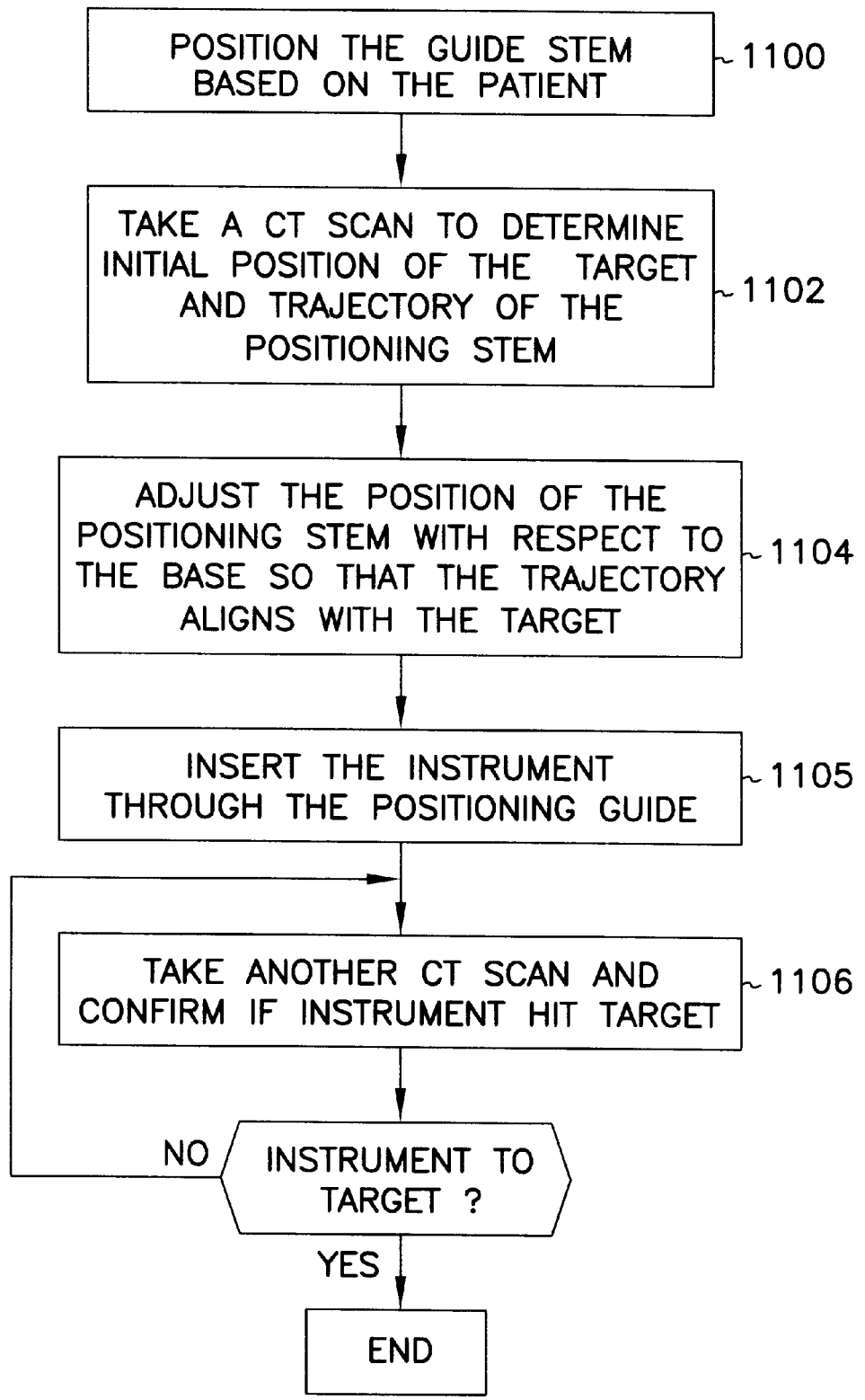
FIG. 11 is a flow chart indicating the steps in using the trajectory guide in a CT scanning environment.

Now turning to FIG. 11, as shown by step 1100, the positioning stem 400 or 400' is initially positioned. As depicted by step 1102, a CT scan is performed to initially locate the positioning stem 400 or 400' and the target 270. The line or trajectory formed by the positioning stem 400 or 400' is read by the CT scanning system 100. The trajectory 260 is determined by determining a line between the end 430 or 430' of the positioning stem 400 or 400' nearest the patient and the target 270. The computer 102 determines the difference between the trajectory 260 and the line formed by the doped positioning stem 400, 400'. The computer 102 determines the adjustment that the surgeon must make to reposition the positioning stem 400 or 400' so that it corresponds to the trajectory 260. The adjustment corresponds to the increments 912, 922 on the arched bails 910, 920 attached to the base 210.

The computer 102 also determines the plane corresponding to the edge of one of the bails 910 or 920. The computer can then output an adjustment that can be made by the surgeon or person doing the procedure. Given the plane defined by the edge of one of the arched bails 910 or 920, the position of the other bail 920 or 910 can be determined.

The physician is instructed to leave one bail 910 in a fixed position. In fact, one bail 910 could remain in a fixed position. The edge of the other bail 910 is moved to a mark 912 on the fixed bail 910. The edge with the markings 922 is moved to a mark 912. The bail 920 is then secured into position. The surgeon then moves the positioning stem 400 or 400' to a mark 922 on the second bail 920 to reposition the positioning stem 400 or 400' so that it corresponds to the trajectory 260. This series of steps corresponds to the step of adjusting the position of the positioning stem so the trajectory aligns with the target 1104.

The instrument is then inserted using the guide stem. In the instance of the trajectory guide 200, the positioning stem is replaced by the guide stem. In the instance of the trajectory guide 200', the positioning stem 400' is removed and then the instrument is placed in the movable member. The instrument is inserted to a selected distance into the patient, as depicted by step 9. The selected distance is the distance to the target 270 along the trajectory 260.

Another CT scan is then done, as depicted by step 1106, to confirm that the instrument is at the target 270. If the instrument has not reached the target 270, the needle is inserted another selected distance (step 1105).

The procedure for repositioning the positioning stem 400 or 400' may be modified slightly depending on the size of the target 270 and whether a burr hole opening will be made. The trajectory guides 200 and 200' do not need a burr hole, but they can be used with burr holes. If a burr hole is formed, the contents within the cranium shift may shift slightly as a result of fluid loss through the burr hole. If the target 270 is large, such as a tumor, it may not be necessary to recheck the trajectory 260. If the target is small, it may require a recheck of the trajectory even if only a twist drill opening is made in the skull.

Frameless Stereotaxy Environment

Figure 12:
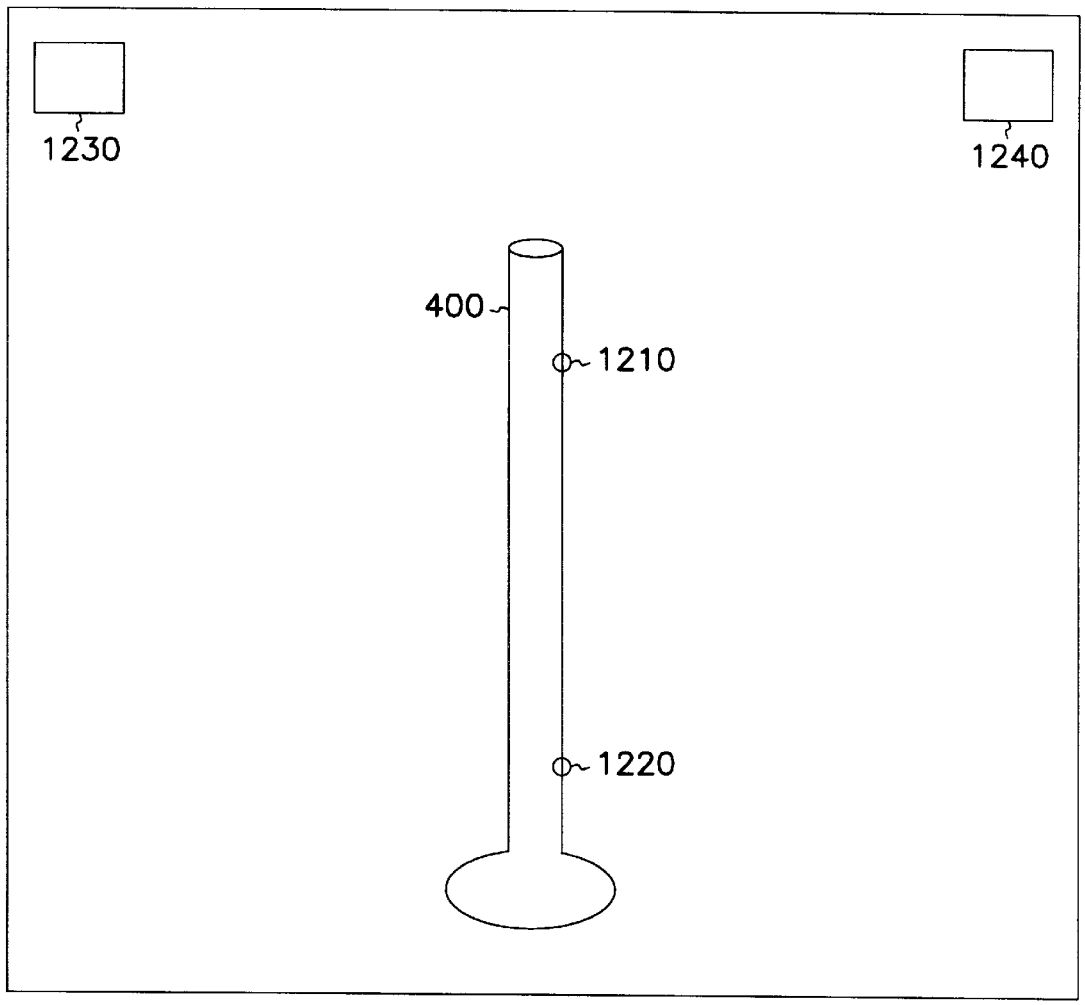
FIG. 12 is a side view of the positioning stem of the trajectory guide which includes light emitting diodes.

In an environment where there are detectors for light-emitting diodes ("LEDs"), the trajectory guide 200 as shown in FIG. 4 or the trajectory guide 200' as shown in FIG. 8 can be used to accomplish this procedure. FIG. 12 shows the positioning guide 400 of the trajectory guide 200 provided with two or more LEDs 1210 and 1220 which are located along the length of the positioning stem 400. Rather than use the arched bails 910 and 920 to reposition the positioning stem 400, one or more LED detectors 1230 and 1240 are used to locate the LEDs 1210 and 1220. The step of adjusting the position of the positioning stem 1104 so that it aligns with the trajectory 260 to the target 270 is accomplished by moving the positioning stem 400 manually until the LEDs 1210 and 1220 form a line which is collinear with the trajectory 260. The computer 102 determines the trajectory 260 by determining the formula for a line between the target 270 and the end of the positioning stem 400 closest to the patient. The positioning stem 400 is moved until the LEDs 1210 and 1220 are aligned with the trajectory 260. The positioning stem can be moved manually (directly or remotely) or by automated control, such as under control of a computer. The LED's position can be determined by the detectors 1230 and 1240 at a relatively high frequency rate such that movement of the positioning stem 400 can be monitored in real time. Once the LEDs 1210 and 1220 are aligned with the trajectory 260, the computer 102 will output a signal indicating that the positioning stem 400 is correctly positioned. The same procedure would be followed for a trajectory guide 200'. The positioning stem 400' would be provided with the LEDs 1210 and 1220. Once the positioning stem 400' is correctly positioned, a signal from computer 102 indicates the correctly positioned positioning stem 400'. The movable member 820 is then locked into position. The positioning stem 400' is removed and the instrument is passed into the opening 822 in the movable member 820.

Of course, this procedure may be modified slightly depending upon the particulars of the procedure. The trajectory guides 200 and 200' do not need a burr hole, but can be used with burr holes. If a burr hole is formed during the procedure, the contents of the cranium shift slightly as a result of fluid loss through the burr hole. If the target 270 is large, such as a tumor, it may be unnecessary to recheck the trajectory 260. If the target is small, such as when the target is the globus pallidus interna, it may be necessary to recheck the trajectory before inserting a tool or an instrument to the target 270. Once the trajectory 260 is determined, the instrument or tool is inserted a selected distance into the trajectory guide 200 or 200'. The selected distance is equal to the distance between the trajectory guide and the target 270. The position of the instrument or tool can then be checked using x-radiation to determine if the tool or instrument has reached the target 270.

Magnetic Resonance Imaging Procedure

The trajectory guide 200 or 200' can also be used in an MR imaging environment. In such an environment, the positioning stem 400 or 400' is provided with a dopant that can be read by an MR imaging device. The procedure set forth above for the frameless stereotaxy environment is similar to the procedure used here. The MR imaging device is used to determine the position of the positioning stem 400 and to determine the trajectory between the portion of the positioning stem nearest the patient and the actual target 270. The positioning stem 400 is moved either manually or with the aid of a remote device. The positioning stem 400 is moved until it is positioned so that it is collinear with the trajectory 260 between target 270 and the end of the positioning stem 400 nearest the patient.

The basic procedure set forth in FIG. 11 varies at a step 1104, which is to adjust the position of the positioning stem. When using CT scanning equipment only, the positioning stem 400 is adjusted using the arched bails 910 and 920. When the trajectory guide is used in an MR environment, the MR scanning device is used to locate the position of the positioning stem 400. In either environment, the positioning stem 400 may be used in association with frameless stereotaxy, in which case LED detectors are used to find the position of the positioning stem. Once the positioning stem is properly located collinearly with the trajectory 260, the instrument is inserted through the trajectory guide 200 or 200' toward the target 270 to a specific distance. Another scan is then taken to confirm that the instrument is at the target. These are the steps as shown and described previously and correspond to steps 1106 and 1108 in FIG. 11.

Figure 13:
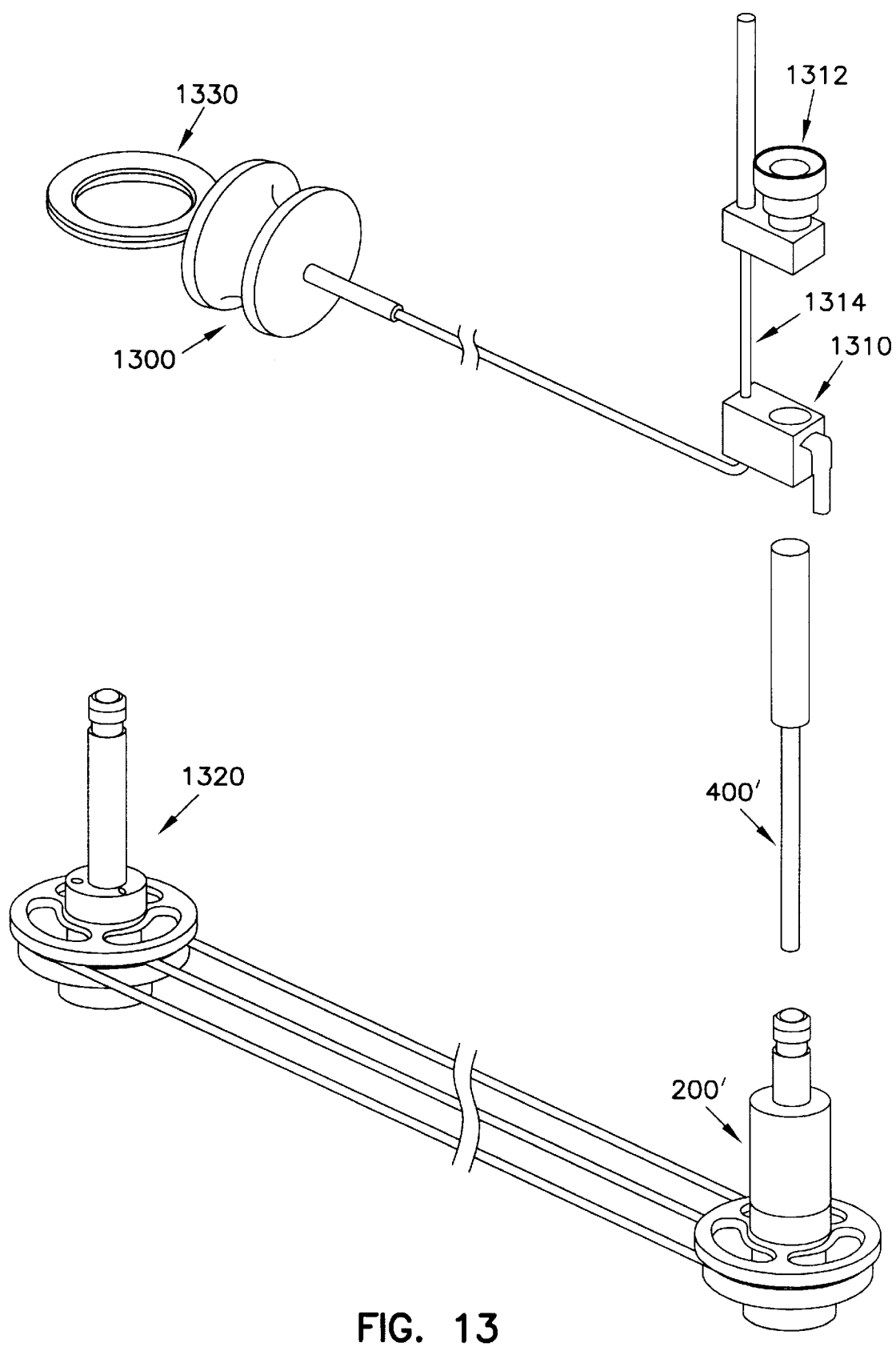
FIG. 13 is a remote system to allow a person to operate the trajectory guide from outside a scanning environment.

FIG. 13 shows a remote controlled version of trajectory guide 200' that could be used under MR guidance. The remote device includes a remote positioner 1320 which either duplicates the trajectory guide 200' or the movement of the trajectory guide 200'. The replica trajectory guide 1320 is manipulated until the positioning stem 400' is located collinearly with the trajectory 260 to the target 270. (The trajectory 260 and the target 270 are shown in FIG. 2.) The positioning stem 400' is then removed from the trajectory guide 200' and an instrument is placed into the trajectory guide 200'. Attached to the instrument is a block 1310 and a locking collar 1312. A rod member 1314 is attached between the block 1310 and the locking collar 1312. The locking collar 1312 holds the instrument by coiling around the stem of a surgical instrument or tool. Pulling a plunger 1330 causes the locking collar to move toward the block 1310, thereby inserting the tool or instrument through the trajectory guide 200' to the target 270. Once the instrument tip reaches the target 270 within the patient, the locking collar and block can be removed and the procedure, such as a biopsy or laser ablation, can be performed.

Burr Hole Externalizer Adapter for Other Tools

Figure 14:
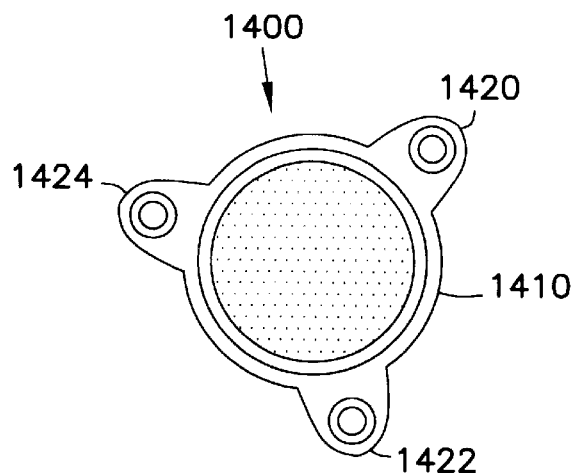
FIG. 14 is a top view of a burr hole extension apparatus.
Figure 15:
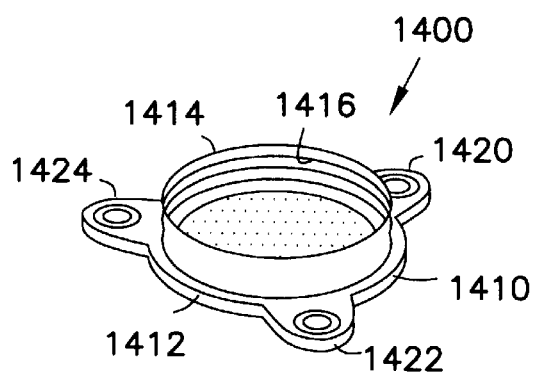
FIG. 15 is a side view of the burr hole extension apparatus shown in FIG. 14.
Figure 16:
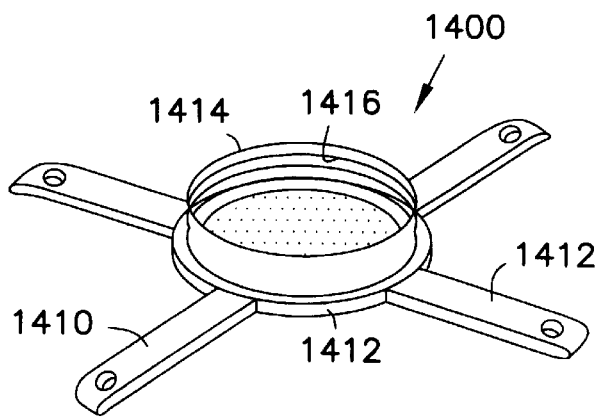
FIG. 16 is a top view of another embodiment of the burr hole extension apparatus.

Turning now to FIGS. 14–16, the burr hole externalizer will be detailed. FIG. 14 is a top view of a burr hole extension apparatus 1400. FIG. 15 is a side view of the burr hole externalizer 1400. The burr hole externalizer 1400 is made of a tubular body 1410 with a set of flanges 1420, 1422, and 1424 attached thereto. The tubular body 1410 is approximately 1 cm in height. The tubular body 1410 has a height that allows clearance between the tubular body and the tool to allow insertion of the tool into the patient's body. The tubular body 1410 has a flange end 1412 and a burr hole end 1414. The flanges 1420, 1422, and 1424 are used to attach the burr hole externalizer 1400 to the patient. The flanged end 1412 is the end of the burr hole externalizer 1400 that contacts the patient. The burr hole end 1414 is positioned a distance from the patient's body. The burr hole externalizer 1400 basically provides a substitute opening for a burr hole that used to have to be made in the patient. The burr hole end 1414 of the tubular body is dimensioned so that it replicates a burr hole. The inner diameter of the burr hole end 1414 is the same as a standard burr hole. It should be pointed out that the Europeans have one standard diameter and the rest of the world has another standard diameter. The burr hole end 1414 may also include an inside thread 1416 so that tools which thread into a burr hole can also thread into the burr hole end 1414 of the externalizer 1400. It should be noted that an inside thread is not necessary. Thus the externalizer 1400 can also be thought of as a universal adapter for tools that normally are attached to a burr hole.

In operation, a physician/surgeon will initially position the burr hole externalizer 1000 onto the patient's body. For the sake of example, the physician surgeon will initially position the externalizer on the patient's head. The burr hole externalizer is held in place using several bone screws. The bone screws pass through openings in each of the flanges 1420, 1422, and 1424. A selected tool is then attached to the burr hole end 1014 of the burr hole externalizer 1400. The tool attached can be a trajectory guide such as described above or such as described in U.S. patent application Ser. No. 08/919,649 filed Aug. 28, 1997 and entitled "Surgical Instrument Trajectory Guide Method and Apparatus". The tool can be any tool that previously required attachment to a burr hole in the body of the patient. The advantages associated with using the burr hole externalizer 1400 stem from the fact that the surgeon no longer has to make a burr hole in the patient. Not having to make a burr hole means that the procedure takes less time. It also results in less fluid loss from the spine and the cranium which results in less shifting of the target or contents of the head. In addition to several small bone screws, the only opening made in the patient's body is a small twist drill hole. A twist drill hole has a diameter of approximately 2 mm. This is much smaller than the 12–15 mm burr hole previously discussed above. A drill hole of this small size can be made with a minor incision or scalp or upper body area and with minimal trauma. Thus, there is less trauma and less discomfort for the patient when the burr hole externalizer is used.

FIG. 16 is a top view of another embodiment of the burr hole externalizer 1400. Most of the components are the same and are numbered the same as the externalizer 1400 shown in FIG. 14. The difference is that the flanges are replaced with a first headband 1610 and a second headband 1612. This produces four long legs when compared to the externalizer 1400 shown in FIG. 14. Three elongated legs could also be used to provide adequete attachment of the externalizer to the patient's body. In the ends of each head band are openings for body screws. The body screws may not have to be used to secure the burr hole externalizer 1400 to the patient. It should be noted that the embodiments shown are just two examples of ways of attaching the burr hole externalizer 1400 to the patient. There are many ways of stably attaching the burr hole externalizer 1400. In addition, although a burr hole is normally used for entering the cranial cavity, this externalizer 1400 could easily be used for similar operations on other portions of the patient's body. Procedures that formerly required many hours can now be performed in substantially less amounts of time with the burr hole externalizer and the trajectory guide 200.

Many uses are contemplated for this new trajectory guide 200. For example, a surgical instrument can be used to access certain portions of the body of the patient. Using the head of a human patient as an example, the trajectory guide 200 can be used to deliver an instrument to an area of the brain for biopsy. An instrument can also be used to access the ventricular area of the brain and cerebrospinal fluid for placement of a ventricular shunt or drain. The trajectory guide can also be used to enable a neurosurgeon to perform ventricular endoscopy. The instrument in such endoscopy typically includes a fiber optic for viewing a portion of the brain. The instrument can be rigid or flexible. The trajectory guide 200 can also be used in treating or researching various other disorders or diseases of the brain, such as Alzheimer's disease, multiple sclerosis, Huntington's chorea, Parkinson's disease and other neurodegenerative diseases. The globus pallidus is one key to controlling the tremors that patients with Parkinson's disease have. In some treatments, electrodes are used to deliver electrical signals to this organ to reduce or eliminate the effect of Parkinson's disease. In addition, a surgical instrument can be used to perform a pallidotomy (i.e., lesion the globus pallidus). Similarly, other targets include the thalamus and subthalamic nucleus. Depending on the surgeon, additional targets could be considered, including nuclear and non-nuclear regions of the brain stem. Another surgical procedure is the removal of tumor material in the brain. The tumor can be located and eliminated using an instrument delivered with the help of the trajectory guide 200. Still other procedures are removal of lesions which are formed in the brain due to strokes or other medical conditions.

Other Uses of the Trajectory Guide

Described above are procedures associated with the head and brain. There are numerous other surgical procedures that can also be performed on other than the brain that would benefit from accurate placement of a surgical tool. In particular, it is anticipated that cardiac and pulmonary conditions will be ameliorated by minimally invasive therapies that can be made possible with the trajectory guide. In such procedures, the trajectory guide is more of a body portal and may or may not be used to lock into a specific trajectory toward a target. Moreover, such procedures may require use of more than one trajectory guide or may require a multiple body portal configuration in which each of the portals include one or more trajectory guides. In such therapies, surgical instruments or observational tools may be inserted to enable the surgeon in performing surgical procedures. Similarly, probes may be delivered to specific targets or general targets by the trajectory guide for the performance of cryotherapy, laser therapy, radio frequency ablation, microwave interstitial therapy, focussed ultrasound therapy and other therapies. These therapies are all currently done on various parts of the body in conjunction with an imaging device, such as the CT scanning device 100. The trajectory guide 200 makes delivery of the instruments to the various targets easier in all of these therapies. In addition, the use of the burr hole externalizer 1000 further speeds procedures that require the entry of tools into the patient's body.

Figure 17:
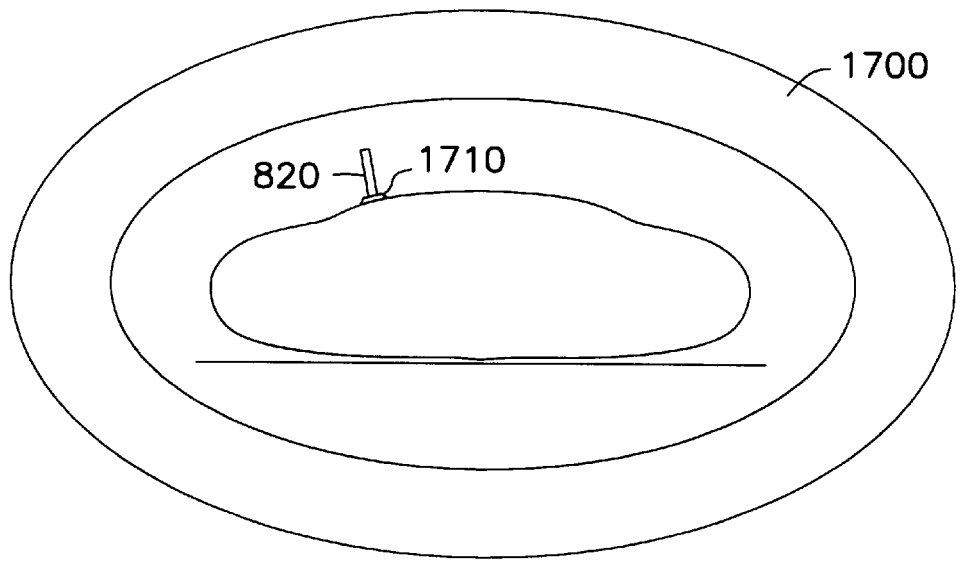
FIG. 17 is an end view of a patient positioned within a magnet having a body type trajectory guide attached thereto.
Figure 18:
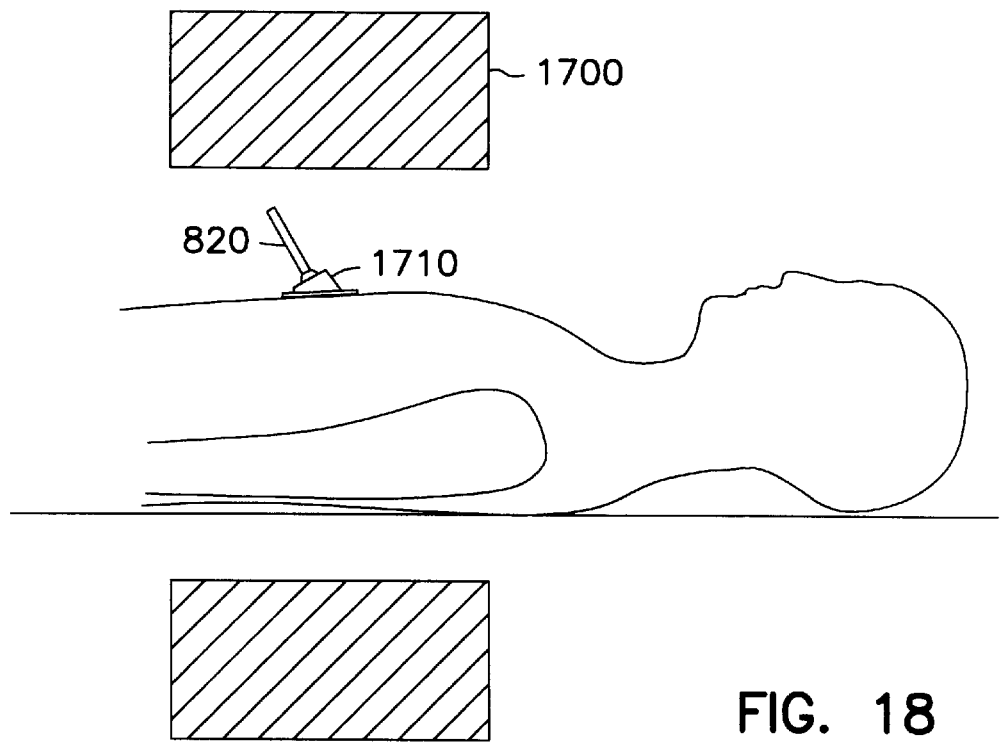
FIG. 18 is a side view of a patient positioned within a magnet having a body type trajectory guide attached thereto.

FIGS. 17–21 show a trajectory guide 1700 which can be used as a body portal. FIG. 17 is an end view of a patient positioned within a MR scanner 1700. The patient has a body portal type trajectory guide 1710 attached and positioned on their body. FIG. 18 is a side view of a patient positioned within a conventional MR scanner 1700. As shown in FIG. 18, the body portal type trajectory guide is positioned at an angle with respect to the body of the patient so that the total overall height of the body portal type trajectory guide 1710 will fit within the conventional MR scanner 1700. The movable element 820, if positioned perpendicular with respect to the body, may interfere with the MR scanner 1700. Most certainly if the movable element 820 is positioned perpendicular with respect to the body, a surgical instrument could not be placed within the movable element 820. A surgical instrument such as a catheter extends through a longitudinal opening or passageway 822 in the movable element 820. When perpendicular to the patient, there would not be enough room between the MR scanner 1700 and the surgical instrument being placed within the passageway 822 of the movable element 820. It should be noted that the body portal type trajectory guide 1710 may be equipped with a movable element 820 or a guide member 240 or a positioning member 400. The movable member 820 is rotatable with respect to the patient so that a surgical instrument may be placed within the movable member 820 from any position the surgeon may take with respect to the patient. In a scanning environment that has an open magnet, an angled base is not necessary. The base for the body portal type positioner could be made with a vertical surface or a surface substantially parallel to the patient's body.

Figure 19:
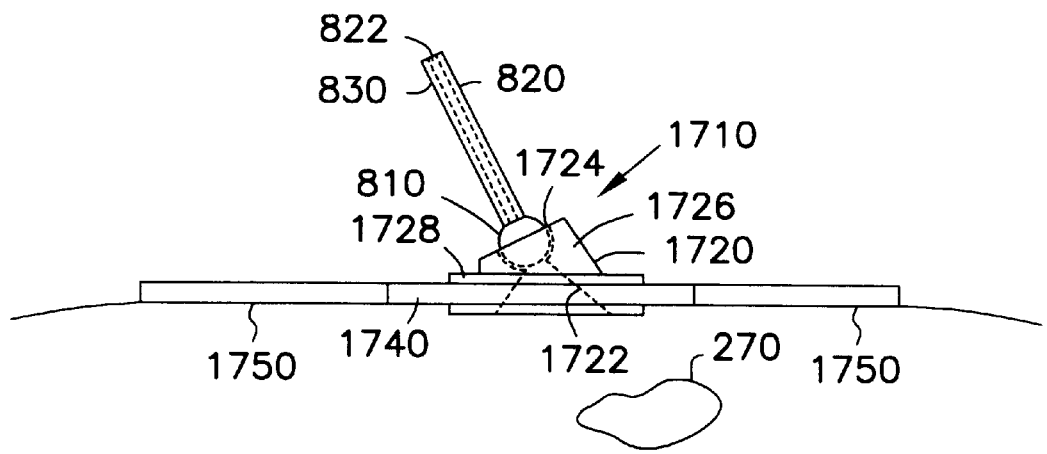
FIG. 19 is a side view of a body type trajectory guide.
Figure 20:
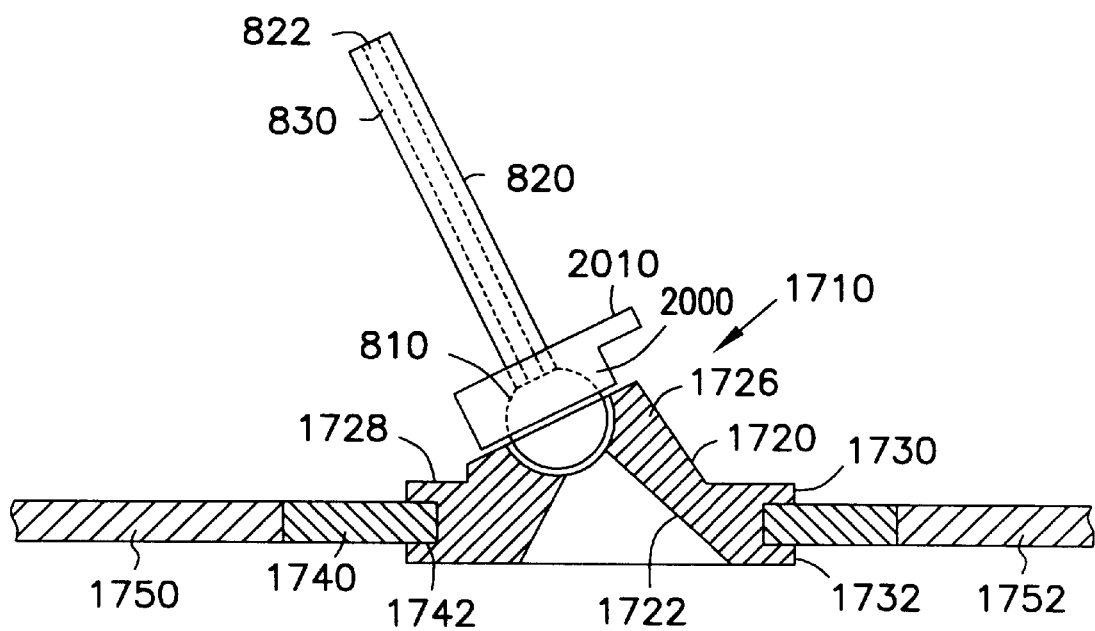
FIG. 20 is a cutaway side view of the body type trajectory guide.
Figure 21:
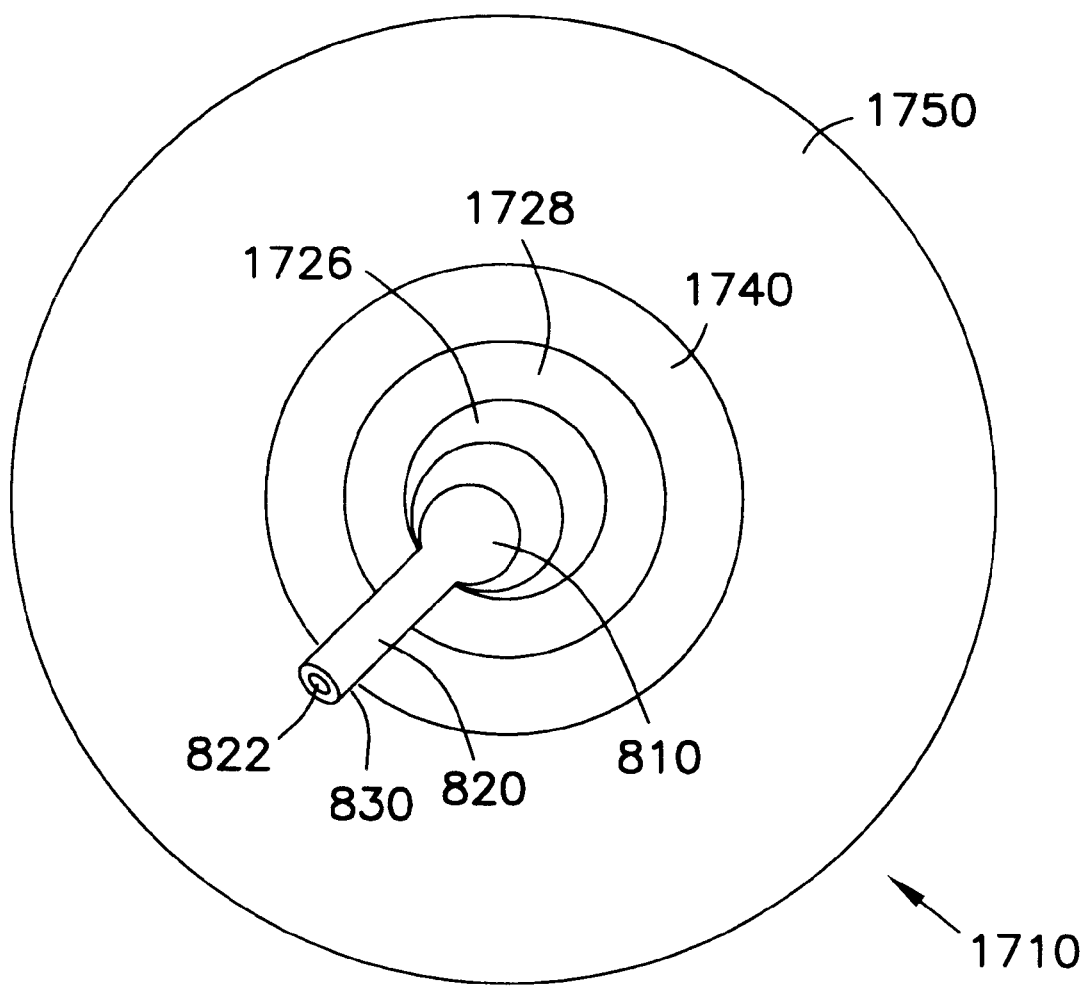
FIG. 21 is a top view of the body type trajectory guide.

FIGS. 19–21 show the body portal type trajectory guide 1710 in more detail. FIG. 19 is a side view of the body portal type trajectory guide 1710 and FIG. 20 is a cutaway side view of the body portal type trajectory guide 1710. The movable element 820 includes passageway 822. The movable element 820 also has a guide stem end 830 and a base end 810. The base end 810 is ball shaped. The body portal type trajectory guide 1710 includes a base 1720 which has an opening or passageway 1722 therein. The passageway 1722 allows the surgical instrument to pass into the body of the patient and to a target 270 within the patient. At one end of the passageway 1722 is a cup 1724. The cup 1724 is dimensioned such that the cup grips the ball end 810 of the positioning member 820. The cup 1724 may also include portions which extend beyond the largest diameter of the ball end 810 to further grip the ball end 810 of the movable member 820. The base 1720 also includes an angled portion 1726 and a flat base portion 1728. The flat base portion 1728 is circular and includes a first flange 1730 and a second flange 1732. A plastic ring 1740 includes a finger 1742 which engages the slot between the first flange 1730 and the second flange 1732 of the flat base. The plastic finger 1742 engages the slot between the first flange 1730 and the second flange 1732 so that the base 1720 can rotate or swivel with respect to the plastic ring 1740. The plastic ring 1740 is merged or attached to a flexible adhesive patch 1750. The flexible adhesive patch is made from a flexible material which can conform to various body portions or parts of a patient. An adhesive material is placed on one side of the flexible adhesive patch. The adhesive is placed on surface 1752 which is opposite the side of the flexible adhesive patch 1750 closest to the angled base portion 1726. The flexible adhesive patch 1750 is made of a biocompatible material such as might be used to affix a colostomy bag to a patient or a similar material. FIG. 21 shows an embodiment that includes a quick locking mechanism 2000. The base is provided with a high pitch thread. The locking mechanism 2000 is provided with a matching high pitch thread. The locking mechanism 2000 is also provided with a single arm or knob 2010 for turning the locking mechanism 2000 with respect to the threaded base portion. The knob 2010 is positioned away from the patient so that the surgeon has easy access to the knob 2010. Because a high pitch thread length is used, the knob needs to be turned only slightly to lock the movable element 820 into position with respect to the base.

FIG. 21 is a top view of the body portal type trajectory guide 1710. The movable member 820 includes the guide stem end 830 and the ball end 810 which is positioned within the cup 1724. The base is angled through the angled base portion 1726 and is attached to the flat base portion 1728. The flat base portion is attached to the plastic ring portion 1740 which in turn is merged with a flexible body patch 1750.

In operation, the body portal type trajectory guide 1710 is used as follows. Initially, the surgeon determines the approximate location of the target 270 within the body of the patient. An incision is made in the patient near the target 270. The body portal type trajectory guide 1710 is then placed over the incision so that the passageway 1722 in the base 1720 is positioned over the incision that is made in the patient. The passageway 1722 is roughly aligned with a line between the target and the incision within the patient. The flexible adhesive patch 1750 is attached to the patient to seal the incision as well as to provide a stable attachment point for the body portal type trajectory guide 1710. The movable member 820 can be repositioned with respect to the cup 1724 within the base 1720 of the trajectory guide 1710. The entire base 1720 can be moved with respect to the plastic ring 1740 and the flexible adhesive patch 1750. By moving the base with respect to the flexible adhesive patch, a surgeon is afforded the flexibility to work from a variety of positions with respect to the patient and with respect to the MR scanner which is positioned around the patient. Initially, the physician will roughly position the base 1720 with respect to the target. The base 1720 can be rotated with respect to the plastic ring and flexible adhesive patch to enable the surgeon to take any position with respect to the incision and the patient. The movable member 822 can then be moved to assure that the surgical instrument that will be placed within the opening or passageway 822 in the movable member 820 will intersect with the target 270. The movable member can be equipped with RF micro coils to aid in positioning the movable member, similar to those described in U.S. patent application Ser. No. 08/919,649 filed Aug. 8, 1997 and entitled "Surgical Instrument Trajectory Guide Method and Apparatus".

It should be noted that the body portal type trajectory guide 1710 will be used when the targets 270 are relatively large. In other words, a trajectory guide 1710 can be used to take a biopsy of a liver, which is a relatively large organ. Thus, if the guide member 820 is slightly out of position, the sample will come from just a slightly different portion of the liver but will still be valid. Although a locking member could be provided, the body portal type trajectory guide 1710 shown does not feature a locking member for the movable member 822. The cup 1724 holds the ball end 810 of the movable member 820 tightly such that it will not move under most conditions. As stated before, the body portal type trajectory guide 1710 is used on relatively large targets 270 and, therefore, slight movement of the movable member due to respiratory excursion will not affect the placement of the surgical instrument within the large target 270. Once the surgical instrument has been inserted through the passageway 822 and the passageway 1722 and to the target 270 and the operation has been performed, the surgical instrument is removed. The body patch 1750 can then also be removed. By removing the body patch 1750, the entire trajectory guide 1710 is also removed. The incision is then sewn or bandaged by the surgeon to end the operation. The main advantages of the body portal type trajectory guide 1710 is that the operation can be done relatively quickly in either a CT or MR environment. The body patch 1750 also keeps the area clear and clean. Operations that used to be difficult or impossible or used to take large amounts of time can now be performed easily and efficiently.

There are many other uses contemplated for the body portal type trajectory guide 1710. The trajectory guide 1710 can be used to biopsy or provide therapy to organs in or near the abdomen or pelvis. Among the uses are liver biopsies, renal biopsies, pancreatic biopsies, adrenal biopsies. In addition, some procedures require both a biopsy as well as a therapy. The biopsy needle is used first and then an instrument used in therapy is substituted for the biopsy needle. The instrument for applying therapy includes instruments for thermal ablation, and instrument for providing shunts to various organs such as TIPS (transjugular intraheptic portal systemic shunts). The trajectory guide 1710 can also be used to conduct biliary drainages, and used to conduct other biopsies and treatments at or near the abdomen of the pelvis. The trajectory guide 1710 can also be used for procedures on the back and near the spine of a patient. Nerve blocks, epidural injections, facet injections, sacroiliac joint injections, and spinal cordotomy are just a few of the procedures possible with the trajectory guide 1710. Non-brain treatments and biopsies in the head and neck can also be accomplished using the trajectory guide 1710. Trigeminal neuralgia can be treated using the trajectory guide 1710. Biopsies of the pleura, the lung, and the mediastinurn and removal of emphazematious blebs to reduce the volume of the lung can be done percutanously using the trajectory guide. The trajectory guide 1710 can also be used for fetal surgery such as for division of fetal hydrocephalus, and for treatment of fetal hydronephrosis. These are just a sampling of the possible procedures that can be done using the body portal type trajectory guide 1710. Numerous other procedures will be accomplished using this device. In addition, the device rise to other future surgical procedures.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A surgical device for use on a patient comprising:
    a unitary base unit having a tubular body, said base unit further comprising:
        a first end; and
        a second end, said tubular body having a seat therein, said seat positioned near said first end, said tubular body having an opening in said second end, wherein the opening in the second end of the tubular body has a sufficient diameter to allow tools to pass through the opening; and
    an attachment mechanism positioned near the second end of the tubular body of the base unit, said attachment mechanism for attaching the base unit to a patient, said seat and said attachment mechanism separated by a distance.

2. The surgical device of claim 1, wherein said attachment mechanism further comprises a flange.

3. The surgical device of claim 1, wherein said attachment mechanism further comprises a flange, said flange having a plurality of openings therein, each opening receiving a fastener.

4. The surgical device of claim 3, wherein the fastener is a bone screw.

5. The surgical device of claim 1 further comprising a movable member which includes a portion which fits within said seat.

6. The surgical device of claim 5 further comprising a positioning stem for moving the movable member.

7. The surgical device of claim 6 wherein the positioning stem includes a mechanism for locating the positioning stem in a CT scanning environment.

8. The surgical device of claim 6 wherein the positioning stem includes a dopant for locating the positioning stem using CT scanning equipment.

9. The surgical device of claim 6 wherein the positioning stem includes a mechanism for locating the positioning stem in a frameless stereotaxy environment.

10. The surgical device of claim 6 wherein the positioning stem includes at least two light emitting diodes for locating the positioning stem in a frameless stereotaxy environment.

11. The surgical device of claim 10 wherein the frameless stereotaxy environment includes at least two detectors for light from light emitting diodes.

12. The surgical device of claim 6 wherein the positioning stem includes a mechanism for locating the positioning stem in a magnetic resonance imaging environment.

13. The surgical device of claim 12 wherein the positioning stem includes a dopant for locating the positioning stem in a magnetic resonance imaging environment.

14. The surgical device of claim 6 wherein the base further includes:
    a first bail attached to said base; and
    a second bail attached to said base, said first and second bail used for repositioning the positioning stem.

15. The surgical device of claim 14 wherein at least one of the first bail or the second bail is rotatably attached to the base unit of the surgical device.

16. The surgical device of claim 14 wherein the first bail includes markings thereon and the second bail includes markings thereon.

17. The surgical device of claim 6 further comprising a remote mechanism for controlling the positioning member from a position away from the positioning member.

18. The surgical device of claim 17 further comprising a locking mechanism for holding an instrument in position, said locking mechanism actuatable from a position remote from the positioning member.

19. The surgical device of claim 17 wherein the locking mechanism for holding an instrument in position includes a locking collar for clamping the surgical instrument.

20. The surgical device of claim 17 wherein the remote mechanism for controlling the positioning member includes a duplicate surgical device remotely located from the positioning member.

21. The surgical device of claim 20 wherein the remote mechanism for controlling the positioning member includes a plunger remotely located from the positioning member.

22. The surgical device of claim 17 further comprising a computer, said computer determining the initial position of the positioning stem and determining a position where the positioning stem is aligned with a trajectory to a target within a patient.

23. The surgical device of claim 5 wherein the moveable member includes a positioning member, said moveable member and the positioning member having openings therein for guiding surgical instruments.

24. The surgical device of claim 5 wherein the moveable member has an opening therein for guiding surgical instruments, a portion of the opening having threads therein, said threaded portion for receiving a positioning member.

25. The surgical device of claim 24 wherein the threaded portion of the moveable member receives a guide stem having an opening therein, the openings in the moveable member and the guide stem for guiding a surgical instrument.

26. The surgical device of claim 5 wherein the positioning stem includes an indicator for locating the positioning stem in a frameless stereotaxy environment.

27. The surgical device for use on a patient of claim 1 wherein the attachment mechanism includes
    a flange positioned near one of the first open end or the second open end of the base having the tubular body, said flange for attaching the base to a patient, said other of the first open end or the second open end of the tubular body having approximately the same diameter as a burr hole, said other end of the first open end or the second open end of the tubular body for receiving a surgical instrument.

28. The surgical device of claim 27, wherein said attachment mechanism further comprises a plurality of openings within the flange, each opening receiving a fastener.

29. The surgical device of claim 28, wherein the fastener is a bone screw.

30. A surgical device for use on a patient comprising:

a base unit having a tubular body, said base unit further comprising:
  a first end; and
  a second end, said tubular body having a seat therein, said seat positioned near said first end, said tubular body having an opening in said second end; and an attachment mechanism positioned near the second end of the tubular body of the base unit, said attachment mechanism for attaching the base unit to a patient, said seat and said attachment mechanism separated by a distance and including a flange positioned near one of the first open end or the second open end of the base having the tubular body, said flange for attaching the base to a patient, said other of the first open end or the second open end of the tubular body having approximately the same diameter as a burr hole, said other end of the first open end or the second open end of the tubular body for receiving a surgical instrument, wherein the second opening includes a inside threaded portion.

31. A surgical device for use on a patient comprising:

a base unit having a tubular body, said base unit further comprising:
  a first end; and
  a second end, said tubular body having a seat therein, said seat positioned near said first end, said tubular body having an opening in said second end; and an attachment mechanism positioned near the second end of the tubular body of the base unit, said attachment mechanism for attaching the base unit to a patient, said seat and said attachment mechanism separated by a distance and including a flange positioned near one of the first open end or the second open end of the base having the tubular body, said flange for attaching the base to a patient, said other of the first open end or the second open end of the tubular body having approximately the same diameter as a burr hole, said other end of the first open end or the second open end of the tubular body for receiving a surgical instrument; and a band, said band attached to said flange, wherein said band is attached to the patient.

32. The surgical device of claim 31, wherein said band has an opening therein for receiving a fastener.

33. A surgical device for use on a patient comprising:

a base unit having a tubular body, said base unit further comprising:
  a first end; and
  a second end, said tubular body having a seat therein, said seat positioned near said first end, said tubular body having an opening in said second end; and an attachment mechanism positioned near the second end of the tubular body of the base unit, said attachment mechanism for attaching the base unit to a patient, said seat and said attachment mechanism separated by a distance and including a flange positioned near one of the first open end or the second open end of the base having the tubular body, said flange for attaching the base to a patient, said other of the first open end or the second open end of the tubular body having approximately the same diameter as a burr hole, said other end of the first open end or the second open end of the tubular body for receiving a surgical instrument; and a first head band; and a second head band, wherein said first and second head band are attached to the patient.

* * * * *